(12) United States Patent
Chung

(10) Patent No.: US 6,444,421 B1
(45) Date of Patent: Sep. 3, 2002

(54) METHODS FOR DETECTING INTERMOLECULAR INTERACTIONS IN VIVO AND IN VITRO

(75) Inventor: Jay H. Chung, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/054,281

(22) Filed: Apr. 2, 1998

Related U.S. Application Data
(60) Provisional application No. 60/080,234, filed on Nov. 19, 1997.

(51) Int. Cl.[7] .................... C12Q 1/68; C12P 21/06; C12P 19/34; C12N 15/63
(52) U.S. Cl. .................. 435/6; 435/69.1; 435/91.1; 435/91.3; 435/91.4; 435/455
(58) Field of Search .................... 435/69.1, 6, 91.1, 435/91.3, 91.4, 455, 468, 471

(56) References Cited

U.S. PATENT DOCUMENTS

| | | | |
|---|---|---|---|
| 5,356,802 A | 10/1994 | Chandrasegaran | 435/199 |
| 5,436,150 A | 7/1995 | Chandrasegaran | 435/199 |
| 5,487,994 A | 1/1996 | Chandrasegaran | 435/199 |
| 5,792,640 A | 8/1998 | Chandrasegaran | 435/199 |
| 5,871,992 A * | 2/1999 | Teebor et al. | 435/199 |
| 5,916,794 A | 6/1999 | Chandrasegaran | 435/199 |
| 5,989,886 A * | 11/1999 | Boeke et al. | 435/199 |

FOREIGN PATENT DOCUMENTS

WO    WO96/20951    7/1996

OTHER PUBLICATIONS

Kim, et al., Proc. Natl. Acad. Sci. USA 93:1156–1160 (1996).
Kim et al., Proc. Natl. Acad. Sci USA 91:883–887 (1994).
Tucker et al., Mol. Cell Biochem 22(2–3):67–77 (1978).
Tucker et al., Mol. Cell Biochem. 23(1):3–16. (1979).
Serpersu et al., Biochemistry 25:68–77 (1986).
Serpersu et al, Biochemistry 28:1539–1548 (1989).
Weber et al. Biochemistry 29:8632–8642 (1990).
Corey et al., Biochemistry 28:8277–8286 (1989).
Li and Chandrasegaran, Proc. Natl. Acad. Sci. USA 90:2764–8 (1993).
Shortle, Gene 22:181–189 (1983).
Serpersu et al., Biochemistry 26:1289–300 (1987).
Ku et al., Bioorg. Med. Chem. 2(12):1413–1415 (1994).
Castanotto et al., Advances in Pharmacology 25:289–317 (1994).
Natsoulis, et al., "Targeting of a nuclease to murine leukemia virus capsids inhibits viral multiplication," 92 *Proc. Natl. Acad. Sci. USA* vol. 92: 364–368 (1995).

* cited by examiner

*Primary Examiner*—Ardin H. Marschel
(74) *Attorney, Agent, or Firm*—Townsend and Townsend and Crew LLP

(57) ABSTRACT

Methods for assessing intermolecular interactions in vivo and in vitro are provided. Methods are provided for detecting protein-DNA interactions in vivo, in which a cell having a chimeric guide endonuclease molecule and a target nucleic acid is provided, and cleavage of the target nucleic acid by the chimeric guide endonuclease molecule is monitored. Cleavage by the chimeric guide molecule corresponds to binding of the guide domain to the target nucleic acid, or to a protein associated with the nucleic acid. The methods of the invention are adapted to cleavage of target nucleic acids, amplification of target nucleic acids, detection of target nucleic acids, screening of genomic target nucleic acid sequences for guide binding domains, and screening for modulators of chimeric guide binding domain activity. Also provided are methods for detecting interactions between other molecules, including hormones and receptors, enzymes and substrates, and the like.

27 Claims, 9 Drawing Sheets

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:1:

AAGGAAAAAA GCGGCCGC                                                      18

(2) INFORMATION FOR SEQ ID NO:2:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:2:

CGTGGTATTC ACTCCAGAGC GATGAAAAC                                          29

(2) INFORMATION FOR SEQ ID NO:3:

(i) SEQUENCE CHARACTERISTICS:
       (A) LENGTH: 41 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:3:

AAGGAAAAAA GCGGCCGCGG CCAATCTACT CCCAGGAGCA G                            41

(2) INFORMATION FOR SEQ ID NO:4:

(i) SEQUENCE CHARACTERISTICS:
       (A) LENGTH: 44 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:4:

AAGGAAAAAA GCGGCCGCAT AAAAGTCAGG GCAGAGCCAT CTAT                         44

(2) INFORMATION FOR SEQ ID NO:5:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:5:

AAGGAAAAAA GCGGCCGCAG CTCTTCCACT TTTAGTGCAT                    40

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CCGGAATTCG CCCAGCCCTG GC                                      22

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GAAACACTTC AGATCTCCCG AGTCACCGC                               29

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = 5'-phosphorylated guanosine"

(xi) SEQUENCE DESCRIPTION: SEQ ID NO:8:

NCGGTGACTC GGGAGATCTG AAGTG                                   25

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GAAACACTTC AGATCTCCCG AGTCACCGC                               29

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CGTGGTATTC ACTCCAGAGC GATGAAAAC                             29

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GTGAATAAAG GCCGGAT                                          17

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

TACGATGCCA TTGGGATATA TCAACGGTGG                             30

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

CGTGGTATTC ACTCCAGAGC GATGAAAAC                              29

(2) INFORMATION FOR SEQ ID NO:14:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

TGAAGACGAA TTCACCGGTG CAACTTCAAC TAAAAAATTA CATAAAGAAC CTGCGACTTT    60

AATTAAAGCG ATTGATGGTG AGACGGT                                       87

(2) INFORMATION FOR SEQ ID NO:15:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

```
GACGACGGAT CCGGAAGCGG CCGCTTGACC TGAATCAGCG TTGTC           45
```

(2) INFORMATION FOR SEQ ID NO:16:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

```
GCAACCCATG GGTTGC                                           16
```

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

```
TGCGGGGACT CGAGTCTGCA                                       20
```

(2) INFORMATION FOR SEQ ID NO:18:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

```
GACCTTTGTA CATTAATTTA ACCGTATCAC CATCAATCGC T               41
```

(2) INFORMATION FOR SEQ ID NO:19:

(i) SEQUENCE CHARACTERISTICS:
        (A) LENGTH: 4627 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

```
CTAAATTGTA AGCGTTAATA TTTTGTTAAA ATTCGCGTTA AATTTTTGTT AAATCAGCTC    60

ATTTTTTAAC CAATAGGCCG AAATCGGCAA ATCCCTTAT AAATCAAAAG AATAGACCGA    120

GATAGGGTTG AGTGTTGTTC CAGTTTGGAA CAAGAGTCCA CTATTAAAGA ACGTGGACTC    180

CAACGTCAAA GGGCGAAAAA CCGTCTATCA GGGCGATGGC CCACTACGTG AACCATCACC    240

CTAATCAAGT TTTTTGGGGT CGAGGTGCCG TAAAGCACTA AATCGGAACC CTAAAGGGAG    300

CCCCCGATTT AGAGCTTGAC GGGGAAAGCC GGACTAGTTA TTAATAGTAA TCAATTACGG    360

GGTCATTAGT TCATAGCCCA TATATGGAGT TCCGCGTTAC ATAACTTACG GTAAATGGCC    420

CGCCTGGCTG ACCGCCCAAC GACCCCCGCC CATTGACGTC AATAATGACG TATGTTCCCA    480

TAGTAACGCC AATAGGGACT TTCCATTGAC GTCAATGGGT GGAGTATTTA CGGTAAACTG    540
```

-continued

```
CCCACTTGGC AGTACATCAA GTGTATCATA TGCCAAGTAC GCCCCCTATT GACGTCAATG    600

ACGGTAAATG GCCCGCCTGG CATTATGCCC AGTACATGAC CTTATGGGAC TTTCCTACTT    660

GGCAGTACAT CTACGTATTA GTCATCGCTA TTACCATGGT GATGCGGTTT TGGCAGTACA    720

TCAATGGGCG TGGATAGCGG TTTGACTCAC GGGGATTTCC AAGTCTCCAC CCCATTGACG    780

TCAATGGGAG TTTGTTTTGG CACCAAAATC AACGGGACTT TCCAAAATGT CGTAACAACT    840

CCGCCCCATT GACGCAAATG GGCGGTAGGC GTGTACGGTG GGAGGTCTAT ATAAGCAGAG    900

CTCGTTTAGT GAACCGTCAG ATCGCCTGGA GACGCCATCC ACGCTGTTTT GACCTCCATA    960

GAAGACACCG GGACCGATCC AGCCTCCGCG GCCGGGAACG TGCATTGGA ACGCGGATTC    1020

CCCGTGCCAA GAGTGACGTA AGTACCGCCT ATAGAGTCTA TAGGCCCACC CCCTTGGCTT    1080

CTTATGCGAC GGATCCCGTA CTAAGCTTGA GGTGTGGCAG GCTTGAGATC TGGCCATACA    1140

CTTGAGTGAC AATGACATCC ACTTTGCCTT TCTCTCCACA GGTGTCCACT CCCAGGTCCA    1200

ACTGCAGCTC GGTTCTATCG ATTAATACGA CTCACTATAG GGCGCGGCCG CGGCGCGCCG    1260

CGATCGCGCC CGGGGACTCG AGTCCTGCAG GCGGCGGTAC TGGTGGAAAT GGCGATGGTA    1320

CCGGTGGCGG TAATGGCGAC GGCACTGGCG GTGGTTCCGG TTCTGGCGGT GGTAATGGTA    1380

CCGGTACTGG CAATGGTGGC GGTGGCACCG GTGCTACCTC CACAAAAAAG CTGCACAAGG    1440

AGCCAGCTAC CCTGATCAAA GCCATCGACG GTGATACAGT TAAACTTATG TACAAGGGCC    1500

AACCAATGAC TTTTAGATTG TTGTTGGTGG GGACCCCTGA AACTAAGCAC CCAAAAAAAG    1560

GCGTCGAAAA GTACGGGCCC GAAGCCTCCG CTTTCACCAA AAAGATGGTG GAGAATGCTA    1620

AGAAGATCGA GGTGGAGTTT GACAAGGGCC AGAGAACAGA TAAATACGGC AGAGGTTTGG    1680

CTTACATCTA CGCCGACGGT AAGATGGTCA ATGAAGCTCT AGTAAGACAG GGCCTTGCTA    1740

AGGTGGCTTA TGTTTACAAA CCTAATAACA CCCACGAACA ACACTTGAGA AAATCCGAAG    1800

CTCAAGCAAA GAAGGAGAAG TTGAATATTT GGTCCGAAGA TAACGCTGAC TCCGGCCAAT    1860

CCGGAGGTGG CTGCTACCCT TACGATGTCC CAGATTATGC TTCTCTTTAG TGGCCGGCCA    1920

AGCTTGTTAA CGCGCGCGGG CCCAACTTGT TTATTGCAGC TTATAATGGT TACAAATAAA    1980

GCAATAGCAT CACAAATTTC ACAAATAAAG CATTTTTTTC ACTGCATTCT AGTTGTGGTT    2040

TGTCCAAACT CATCAATGTA TCTTATCATG TCTGGATCCC CGGGAATTCG GCGCAGCACC    2100

ATGGCCTGAA ATAACCTCTG AAAGAGGAAC TTGGTTAGGT ACCTTCTGAG GCGGAAAGAA    2160

CCAGCTGTGG AATGTGTGTC AGTTAGGGTG TGGAAAGTCC CCAGGCTCCC CAGCAGGCAG    2220

AAGTATGCAA AGCATGCATC TCAATTAGTC AGCAACCAGG TGTGGAAAGT CCCCAGGCTC    2280

CCCAGCAGGC AGAAGTATGC AAAGCATGCA TCTCAATTAG TCAGCAACCA TAGTCCCGCC    2340

CCTAACTCCG CCCATCCCGC CCTAACTCC GCCCAGTTCC GCCCATTCTC CGCCCCATGG    2400

CTGACTAATT TTTTTATTT ATGCAGAGGC CGAGGCCGCC TCGGCCTCTG AGCTATTCCA    2460

GAAGTAGTGA GGAGGCTTTT TTGGAGGCCT AGGCTTTTGC AAAAAGCTTA TCGCGATAAG    2520

AGGATTTTAT CCCCGCTGCC ATCATGGTTC GACCATTGAA CTGCATCGTC GCCGTGTCCC    2580

AAAATATGGG GATTGGCAAG AACGGAGACC TACCCTGGCC TCCGCTCAGG AACGAGTTCA    2640

AGTCTGCATT AATGAATCGG CCAACGCGCG GGGAGAGGCG GTTTGCGTAT GGGCGCTCT    2700

TCCGCTTCCT CGCTCACTGA CTCGCTGCGC TCGGTCGTTC GGCTGCGGCG AGCGGTATCA    2760

GCTCACTCAA AGGCGGTAAT ACGGTTATCC ACAGAATCAG GGGATAACGC AGGAAAGAAC    2820

ATGTGAGCAA AAGGCCAGCA AAAGGCCAGG AACCGTAAAA AGGCCGCGTT GCTGGCGTTT    2880

TTCCATAGGC TCCGCCCCCC TGACGAGCAT CACAAAAATC GACGCTCAAG TCAGAGGTGG    2940
```

| | |
|---|---:|
| CGAAACCCGA CAGGACTATA AAGATACCAG GCGTTTCCCC CTGGAAGCTC CCTCGTGCGC | 3000 |
| TCTCCTGTTC CGACCCTGCC GCTTACCGGA TACCTGTCCG CCTTTCTCCC TTCGGGAAGC | 3060 |
| GTGGCGCTTT CTCATAGCTC ACGCTGTAGG TATCTCAGTT CGGTGTAGGT CGTTCGCTCC | 3120 |
| AAGCTGGGCT GTGTGCACGA ACCCCCCGTT CAGCCCGACC GCTGCGCCTT ATCCGGTAAC | 3180 |
| TATCGTCTTG AGTCCAACCC GGTAAGACAC GACTTATCGC CACTGGCAGC AGCCACTGGT | 3240 |
| AACAGGATTA GCAGAGCGAG GTATGTAGGC GGTGCTACAG AGTTCTTGAA GTGGTGGCCT | 3300 |
| AACTACGGCT ACACTAGAAG GACAGTATTT GGTATCTGCG CTCTGCTGAA GCCAGTTACC | 3360 |
| TTCGGAAAAA GAGTTGGTAG CTCTTGATCC GGCAAACAAA CCACCGCTGG TAGCGGTGGT | 3420 |
| TTTTTTGTTT GCAAGCAGCA GATTACGCGC AGAAAAAAAG GATCTCAAGA AGATCCTTTG | 3480 |
| ATCTTTTCTA CGGGGTCTGA CGCTCAGTGG AACGAAAACT CACGTTAAGG GATTTTGGTC | 3540 |
| ATGAGATTAT CAAAAAGGAT CTTCACCTAG ATCCTTTTAA ATTAAAAATG AAGTTTTAAA | 3600 |
| TCAATCTAAA GTATATATGA GTAAACTTGG TCTGACAGTT ACCAATGCTT AATCAGTGAG | 3660 |
| GCACCTATCT CAGCGATCTG TCTATTTCGT TCATCCATAG TTGCCTGACT CCCCGTCGTG | 3720 |
| TAGATAACTA CGATACGGGA GGGCTTACCA TCTGGCCCCA GTGCTGCAAT GATACCGCGA | 3780 |
| GACCCACGCT CACCGGCTCC AGATTTATCA GCAATAAACC AGCCAGCCGG AAGGGCCGAG | 3840 |
| CGCAGAAGTG GTCCTGCAAC TTTATCCGCC TCCATCCAGT CTATTAATTG TTGCCGGGAA | 3900 |
| GCTAGAGTAA GTAGTTCGCC AGTTAATAGT TTGCGCAACG TTGTTGCCAT TGCTACAGGC | 3960 |
| ATCGTGGTGT CACGCTCGTC GTTTGGTATG GCTTCATTCA GCTCCGGTTC CCAACGATCA | 4020 |
| AGGCGAGTTA CATGATCCCC CATGTTGTGC AAAAAAGCGG TTAGCTCCTT CGGTCCTCCG | 4080 |
| ATCGTTGTCA GAAGTAAGTT GGCCGCAGTG TTATCACTCA TGGTTATGGC AGCACTGCAT | 4140 |
| AATTCTCTTA CTGTCATGCC ATCCGTAAGA TGCTTTTCTG TGACTGGTGA GTACTCAACC | 4200 |
| AAGTCATTCT GAGAATAGTG TATGCGGCGA CCGAGTTGCT CTTGCCCGGC GTCAATACGG | 4260 |
| GATAATACCG CGCCACATAG CAGAACTTTA AAAGTGCTCA TCATTGGAAA ACGTTCTTCG | 4320 |
| GGGCGAAAAC TCTCAAGGAT CTTACCGCTG TTGAGATCCA GTTCGATGTA ACCCACTCGT | 4380 |
| GCACCCAACT GATCTTCAGC ATCTTTTACT TTCACCAGCG TTTCTGGGTG AGCAAAAACA | 4440 |
| GGAAGGCAAA ATGCCGCAAA AAAGGGAATA AGGGCGACAC GGAAATGTTG AATACTCATA | 4500 |
| CTCTTCCTTT TTCAATATTA TTGAAGCATT TATCAGGGTT ATTGTCTCAT GAGCGGATAC | 4560 |
| ATATTTGAAT GTATTTAGAA AAATAAACAA ATAGGGGTTC CGCGCACATT TCCCCGAAAA | 4620 |
| GTGCCAC | 4627 |

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

| | |
|---|---:|
| CCATGGNNNN NNNNN | 15 |

(2) INFORMATION FOR SEQ ID NO:21:

(i) SEQUENCE CHARACTERISTICS:
        (A) LENGTH: 11 base pairs (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:21:

NNNNNCCATG G                                                          11

(2) INFORMATION FOR SEQ ID NO:22:

(i) SEQUENCE CHARACTERISTICS:
        (A) LENGTH: 201 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1..97
        (D) OTHER INFORMATION: /product= "OTHER"
            /note= "Gly at positions 1-97 may be
            present or absent"

(ix) FEATURE:
        (A) NAME/KEY: Modified-site
        (B) LOCATION: 105..201
        (D) OTHER INFORMATION: /product= "OTHER"
            /note= "Gly at positions 105-201 may be
            present or absent"

(xi) SEQUENCE DESCRIPTION: SEQ ID NO:22:

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
            35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
65              70                  75                  80

Gly Gly Gly Gly Gly Gly Gly Gly Gly Gly Gly Gly Gly Gly Gly
            85                  90                  95

Gly Gly Gly Gly Pro Gly Gly Gly Gly Gly Gly Gly Gly Gly Gly
            100                 105                 110

Gly Gly Gly Gly Gly Gly Gly Gly Gly Gly Gly Gly Gly Gly Gly
            115                 120                 125

Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
            165                 170                 175

Gly Gly Gly Gly Gly Gly Gly Gly Gly Gly Gly Gly Gly Gly Gly
            180                 185                 190

Gly Gly Gly Gly Gly Gly Gly Gly Gly
            195                 200

METHODS FOR DETECTING INTERMOLECULAR INTERACTIONS IN VIVO AND IN VITRO

CROSS REFERENCE TO RELATED APPLICATIONS

This application claims priority to U.S. patent application Ser. No. 08/826,622, filed Apr. 3, 1997, which was converted to provisional application Ser. No. 60/080,234 by way of petition filed on Nov. 19, 1997. This application is also related to co-filed U.S. patent application by Jay Chung entitled "Chimeric Endonucleases for Detecting Protein-nucleic Acid Interaction In Vivo and In Vitro," filed Apr. 3, 1997, Ser. No. 08/825,664, which was converted to provisional application Ser No. 60/113,669 by way of petition filed on Nov. 19, 1997, and to co-filed patent application Ser. No. 09/054,231 by Jay Chung entitled "Chimeric Endonucleases For Detecting Intermolecular Interactions In Vivo And In Vitro", filed on Apr. 2, 1998 as These applications are incorporated by reference in their entireties for all purposes.

FIELD OF THE INVENTION

This invention pertains to the field of detecting intermolecular interactions in vivo and in vitro using chimeric endonucleases that include a nuclease cleavage domain that is linked to a moiety that is capable of directly or indirectly binding to a molecule of interest. The provided chimeric endonucleases are useful for determining the location at which a protein becomes associated with a nucleic acid or other molecule.

BACKGROUND OF THE INVENTION

Molecular interactions form the basis of many biological and chemical events. These include enzymatic reactions, hormone-ligand interactions, drug or toxin-protein interaction and other protein-protein, protein-nucleic acid, and nucleic acid-nucleic acid interactions. Therefore, in order to understand these biological and chemical events, the ability to detect contact or close proximity between two known molecules would be of great value.

The techniques to visualize a protein complex formed on a particular nucleic acids sequence, such as the electrophoretic mobility shift assay (EMSA) and footprinting assays, in vitro and in vivo, have been crucial to understanding how transcription occurs. Present techniques, however, have serious limitations. In a living cell, transcription happens in a far more complex environment than can be duplicated in vitro and as a result, in vitro techniques will not always depict accurately the situation in vivo. For example, in vitro techniques have not been useful in studying long range interactions (>1 kb) such as that of the β-globin LCR which play an important role in transcription in a living cell. In vivo footprinting, on the other hand, reflects protein-DNA interactions in a living cell, but the identity of the complex creating the footprint is not known.

Hybrid affinity cleaving proteins composed of a DNA binding domain of a protein and a Fok 1 endonuclease have been used in vitro for cleavage of nucleic acids in a variation of in vitro footprinting methods. See, Chandrasegaran, U.S. Pat. Nos. 5,487,994 and 5,436,150; Kim et al. (1996) *Proc. Natl. Acad. Sci. USA* 93: 1156–1160 and Kim et al. *Proc. Natl. Acad. Sci. USA* (1994) 91: 883–887. However, here again, it has typically been assumed that the DNA binding domain is sufficient to confer sequence specific binding, and therefore only the DNA binding domain of the transcription factor has been included in the hybrid protein. In vitro, this assumption may be correct, since there are no other proteins present when the hybrid protein binds to the DNA. However, this assumption may not apply in vivo, and may not provide a realistic assessment of the nature of an in vivo DNA-protein complex. Furthermore, these methods do not provide any way of assessing the interaction of proteins which bind indirectly to a nucleic acid, such as proteins which form a transcription initiation complex.

Previously available methods of detecting interactions between molecules in the context of cells or organisms have been hampered by a lack of resolution and insufficient sensitivity. With the current state of the art technique, which combines confocal microscopy and immunofluorescence, two molecular species can be visualized simultaneously. If the two molecular species interact, their fluorescent signals should colocalize. However, because the limit of the resolution for light microscopes is in the order of microns, the two molecular species could be quite far apart in molecular terms and still appear to colocalize. In addition, because fluorophores are directly conjugated to the antibodies in conventional immunofluorescence, there is no way to amplify the signal in a manner analogous to the amplification that occurs when horse radish peroxidase or alkaline phosphatase conjugated antibodies are used. As a result, the sensitivity of the conventional immunofluorescence is limited.

New techniques which provide ways of assessing in vivo nucleic acid-protein, protein-protein, and other intermolecular interactions would be desirable, because they would provide new tools for studying gene regulation, enzymatic reactions, hormone-receptor interactions, and other cellular processes in vivo. In addition to the value that such new methods would bring to basic research, the ability to assess accurately in vivo nucleic acid-protein interactions could provide tools for isolating genes, identifying transcription factors, identifying regulatory regions, identifying transcription factor modulating agents and the like. The present invention provides, inter alia, new methods for assessing in vivo DNA-protein interactions, in vivo RNA-protein interactions, indirect protein-nucleic acid interactions and the like, thereby providing new tools for studying gene regulation, isolating genes, identifying transcription factors, identifying transcription factor modulating agents, identifying regulatory regions and many other features which will become apparent upon further reading. Also provided are new methods for visualizing other types of intermolecular interactions with high resolution and sensitivity.

SUMMARY OF THE INVENTION

The present invention provides methods which provide in vivo procedures for assessing protein-nucleic acid interactions. These methods represent a novel technology referred to generally as Protein Position Identification with Nuclease Tail or "PINPOINT" methods. In the methods, a fusion partner which binds directly or indirectly to a target nucleic acid is fused, typically via a linker, to an endonuclease domain which cleaves the target nucleic acid. By monitoring the in vivo cleavage of the target nucleic acid by the endonuclease domain, it is possible to quantitatively and qualitatively monitor interactions between proteins and nucleic acids, between protein complexes and nucleic acids, and between individual members of a protein complex and a nucleic acid. These methods are adapted to basic research, drug screening methods, methods of finding targets for transcription factors such as oncogenes, methods of finding transcription factors for target sequences, and the like.

The present invention further provides methods of screening test nucleic acids for in vivo binding sites which are cleaved by a chimeric guide endonuclease fusion molecule. Typically, a cell comprising a chimeric nucleic acid encoding the chimeric molecule and a test nucleic acid is provided, the chimeric nucleic acid is expressed in the cell, thereby producing a chimeric guide protein in the cell and, the cell is incubated under conditions in which the guide protein is active.

In one assay of the invention, the test nucleic acid includes a promoter sequence operably linked to a reporter gene. Detection of the presence or absence of reporter gene expression is an indicator for whether the test nucleic acid comprises an in vivo binding site for the chimeric guide molecule. In one class of embodiments, the cell is provided by co-transducing the cell with a plasmid encoding the target nucleic acid and a plasmid encoding a chimeric guide protein. Optionally, one or more additional plasmids comprising one or more additional test nucleic acids are also transduced into the cell, and the effect of the chimeric guide molecule is assessed simultaneously on more than one test nucleic acid. Parallel screening formats are provided, in which a second cell comprising a second chimeric nucleic acid encoding a second chimeric guide molecule and a second test nucleic acid is provided. The second chimeric nucleic acid is expressed and the effect of the chimeric nucleic acid on the second test nucleic acid is monitored.

The invention provides methods of detecting and assessing a nucleic acid binding molecule modulating agent. In the methods, a cell comprising a test nucleic acid binding site (e.g., a promoter sequence which is bound by a transcription factor) and a chimeric guide-endonuclease molecule is provided. The cell is contacted with the potential modulating agent, and the rate of cleavage of the test nucleic acid binding site by the chimeric molecule in the presence of the agent in measured. In one class of embodiments, the invention provides methods of cleaving target nucleic acids in vitro or in vivo. In the methods, a target nucleic acid is contacted by a guide-micrococcal endonuclease fusion molecule in the presence of calcium. The guide-micrococcal endonuclease fusion then cleaves the target nucleic acid. In one embodiment, the cleavage is performed in situ, e.g., in a tissue or cell sample on a solid substrate such as a microscope slide.

The present invention also provides methods for assessing intermolecular interactions both in vivo and in vitro. These methods represent a novel technology referred to generally as "FLASHPOINT" methods. In these methods, which are useful for detecting whether a first molecule is in close proximity to a second molecule, a molecular beacon is attached to the first molecule. The molecular beacon, which can be attached directly or indirectly to the first molecule, is typically an oligonucleotide to which is attached a fluorophore and a quencher. A chimeric endonuclease is attached to the second molecule, either directly or indirectly. To determine whether the first molecule is in close proximity to the second molecule, one detects whether fluorescence is emitted by the fluorophore.

Fluorescence emission is indicative of cleavage of the oligonucleotide by the endonuclease moiety, thereby causing separation of the fluorophore and the quencher. In a preferred embodiment, the endonuclease moiety is inducible (e.g., calcium inducible).

In another embodiment, the invention provides methods of obtaining increased sensitivity in assays such as immunoassays. The methods involve detecting a target molecule by contacting the target molecule with a chimeric endonuclease. The target molecule and the chimeric endonuclease are placed under conditions conducive to formation of an association between the target molecule and the chimeric endonuclease. The chimeric endonuclease is then contacted with a molecular beacon that is composed of an oligonucleotide to which is attached a fluorophore and a quencher. The presence or absence of a fluorescent signal is then detected. A signal, if present, results from cleavage of the oligonucleotide by the endonuclease, which causes separation of the quencher from the fluorophore.

DEFINITIONS

Figure 1:
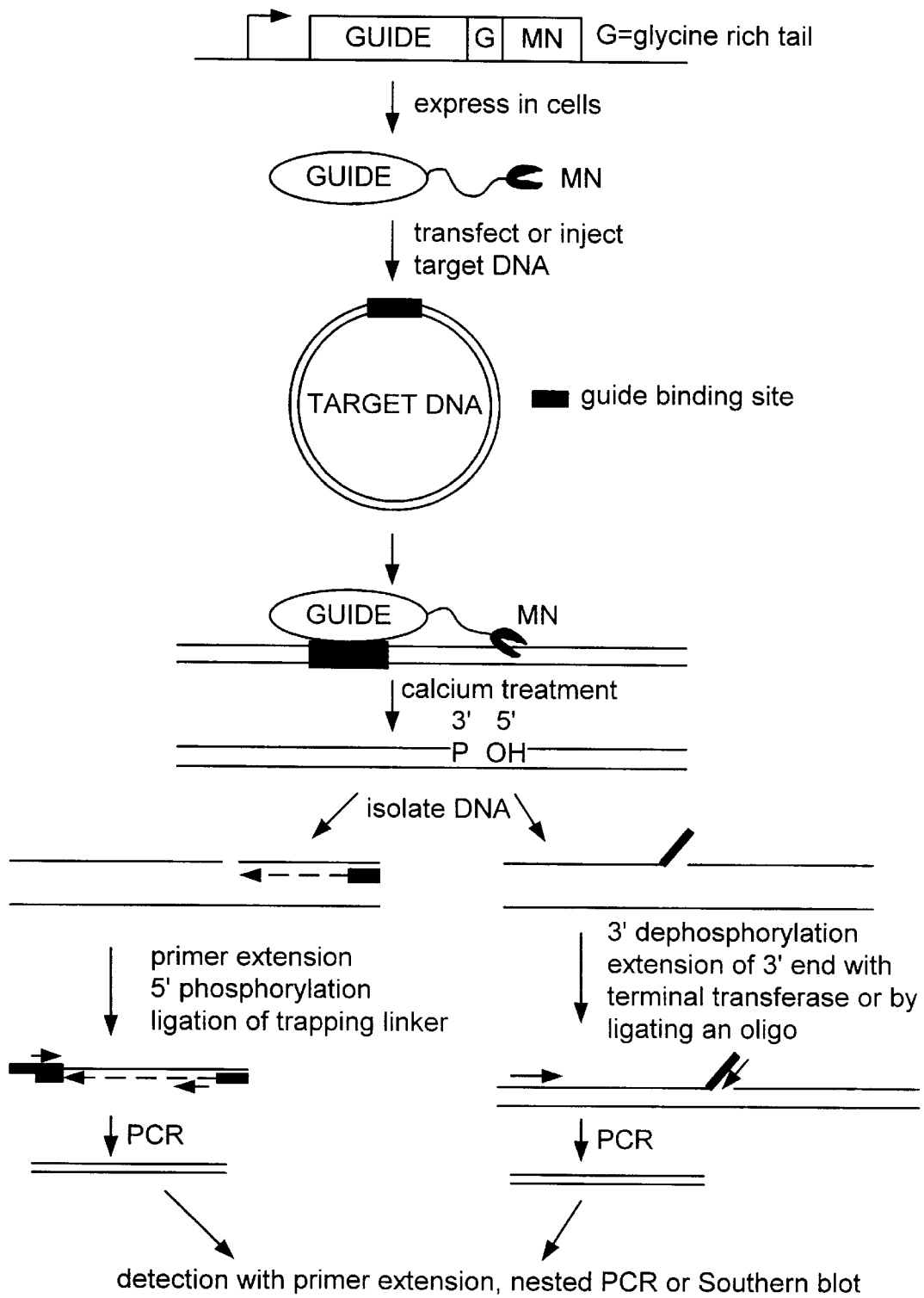
FIG. 1 is a schematic drawing of a method of detecting a plasmid target nucleic acid in vivo.

A "chimeric guide endonuclease fusion molecule" is a molecule with an endonuclease activity domain fused to a guide domain which recognizes either a site on a target nucleic acid, or a site on a molecule such as a protein which binds (directly or indirectly) to a target nucleic acid. The guide and endonuclease domains are optionally separated by a linker region. Guide domains are often polypeptides, but are optionally other molecules which bind directly or indirectly to a target nucleic acid. For example, the guide domain is optionally a nucleic acid which hybridizes to the target nucleic acid. Typical guide domains are derived, inter alia from DNA binding proteins, RNA binding proteins, proteins which bind to DNA binding proteins, proteins which bind to RNA binding proteins, antibody proteins which binds to DNA binding proteins, antibody proteins which bind to antibody proteins which bind to a nucleic acid binding proteins, and the like. An endonuclease domain is typically a polypeptide sequence with endonuclease activity, although other molecules with endonuclease activity (such as RNA ribozymes) can also be used. Preferred endonuclease domains are inducible, rather than constitutive. Examples include micrococcal nuclease and micrococcal endonuclease mutants which have lowered constitutive activity relative to a wild-type micrococcal endonuclease enzyme. In some embodiments, endonuclease domains are recombinantly derived from naturally occurring proteins which have endonuclease activity and are recombinantly fused to the guide domain by making a nucleic acid encoding the endonuclease domain and a nucleic acid encoding the guide domain, and expressing the nucleic acid. In other embodiments, the chimeric guide endonuclease is made by chemically coupling the guide domain and the endonuclease domain. A chimeric guide endonuclease fusion protein is also referred to as a "pointer," for its ability to create a cleavage site or "point" in the target nucleic acid.

The term "nucleic acid" refers to a deoxyribonucleotide (DNA) or ribonucleotide (RNA) polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence optionally includes the complementary sequence thereof. A "target nucleic acid" is a nucleic acid to be cleaved by a chimeric guide-endonuclease fusion molecule. The cleaved target nucleic acid is optionally a DNA an RNA, a combination thereof, or an analogue thereof, and can be in single-stranded or double stranded form, and the cleaved nucleic acid can be modified by a polymerase, by amplification, by ligation of oligonucleotides, or the like. Essentially any nucleic acid can be a target nucleic acid, including chromosomal sequences, extragenomic DNA, plasmids, genomic sequences and the like. The sequence of the target nucleic acid can be known or unknown. The cleavage site made by a chimeric guide endonuclease fusion molecule on the target nucleic acid is referred to as a "target cleavage site" or a "point" i.e., in reference to cleavage by a "pointer."

A cell is "transduced" with a nucleic acid when the nucleic acid is introduced into the cell. A cell is "stably transduced" with a nucleic acid when the nucleic acid is stably replicated in a population of cells.

Two nucleic acids are "ligated" together when one or more covalent bond is formed between the nucleic acids. Ordinarily, nucleic acids are ligated enzymatically, i.e., using a ligase enzyme; however, they are optionally ligated using chemical reagents.

A nucleic acid "tag" is a short nucleic acid of known sequence which is ligated to one or more nucleic acids. A nucleic acid with a ligated tag is a "tagged nucleic acid."

An "internal prime" is a primer (a single-stranded nucleic acid which is typically between 8 and 100 nucleotides in length, usually between 12 and 40 nucleotides in length and often between 17 and 30 nucleotides in length) which hybridizes to a subsequence found between the ends of a nucleic acid.

A "nucleic acid template" or "template" is a nucleic acid which is copied, or, when single stranded, a nucleic acid which is used to make a complementary nucleic acid.

A "terminal region" of a nucleic acid refers to a subsequence of the nucleic acid which is located adjacent to either the 5' or 3' end of the nucleic acid.

A "marker nucleic acid" is a nucleic acid encoding a selectable component. A selectable component is a protein or nucleic acid which either increases or decreases the survival of a cell under selected conditions, or which provides a detectable label which can be used to isolate or identify the cell. For example, the component can encode a component which permits the cell to survive under controlled environmental conditions (e.g., an antibiotic resistance gene permits a cell to replicate in the presence of the antibiotic).

Alternatively, the component can be a molecular tag which facilitates isolation and/or identification of the cell (e.g., a fluorescent protein such as green fluorescent protein (GFP) which permits separation of cells expressing the protein using a fluorescence activated cell sorter (PACS) machine, or using HOOK selection, available from Clontech).

A nucleic acid is "amplified" when corresponding RNA or DNA nucleic acid copies of all or a portion of the nucleic acid are made. The copies of an RNA are optionally RNA or corresponding DNA, and the copies of a DNA are optionally DNA copies or corresponding RNA copies. Copies are made using in vitro techniques such as PCR, LCR, replicase mediated replication, reverse transcription or the like, or are made by cloning the nucleic acid in a cell.

A "calcium inducible" enzyme is an enzyme which has increased activity in the presence of calcium. Typically, the activity increases at least 100% in the presence of calcium, generally at least 500%, commonly 1,000% percent and often at least about 10,000%.

A "micrococcal nuclease" domain is a polypeptide derived from the cleavage domain of micrococcal (or "staphylococcal") nuclease. The polypeptide will have sequence similarity to the naturally occurring nuclease enzyme, but optionally comprises deletions, insertions or other mutations which modulate the activity of the enzyme. Many such modifications of wild-type micrococcal nuclease are known. A particularly useful micrococcal nuclease domain has lower constitutive activity than the wild-type enzyme.

Micrococcal endonuclease produces a 5' OH and a 3' P at the site of cleavage by the enzyme. Although the enzyme typically produces single-stranded nicks in a double-stranded DNA, the enzyme also produces double stranded cuts in the DNA under some reaction conditions. Reviews of micrococcal nuclease activity include Tucker et al. (1978) *Mol. Cell Biochem.* 22(2–3):67–77 and Tucker et al. (1979) *Mol. Cell Biochem.* 23(1):3–16.

Micrococcal endonuclease mutants are described by Serpersu et al. (1987) *Biochemistry* 26: 1289; Serpersu et al. (1986) *Biochemistry* 25:68–77; Serpersu et al. (1989) *Biochemistry* 28:1539–1548 and Serpersu et al. (1990) *Biochemistry* 29:8632–8642. Sequences of micrococcal nuclease are found in available databases, and in, e.g., Shortle (1983) *Gene* 22: 181–189.

A "class I restriction site" is a site on a nucleic acid which, when in double-stranded form, is recognized by a class I restriction endonuclease. A "class IIS restriction site" is a site on a nucleic acid which, when in double-stranded form, is recognized by a class IIS restriction endonuclease. Descriptions of Class I and Class IIS restriction enzymes are found in Berger supra at chapter 11 and in Sambrook and Ausubel both infra. A Class IIS restriction enzyme cleaves a nucleic acid at a site separate from the recognition site for the enzyme. A class II recognition site is a site on a nucleic acid which, when in double-stranded form, is recognized by a class II restriction endonuclease.

Nucleic acids are "concatemerized" when similar or identical nucleic acids are joined, covalently, or non-covalently.

An "oligonucleotide" is a nucleic acid (DNA, RNA or analogue thereof) in single stranded or double stranded form. Typically, the oligonucleotide is less than about 100 nucleotides in length, although longer nucleic acids are also considered oligonucleotides for purposes of this disclosure.

A "recombinant nucleic acid" comprises or is encoded by one or more nucleic acids which are derived from a nucleic acid which was artificially constructed. For example, the nucleic acid can comprise or be encoded by a cloned nucleic acid formed by joining heterologous nucleic acids as taught, e.g., in Berger and Kimmel, *Guide to Molecular Cloning Techniques, Methods in Enzymology* volume 152 Academic Press, Inc., San Diego, Calif. (Berger) and in Sambrook et al. (1989) *Molecular Cloning—A Laboratory Manual* (2nd ed.) Vol. 1–3 (Sambrook). Alternatively, the nucleic acid can be synthesized chemically.

A "primer extension reaction," is performed by hybridizing a primer to a template nucleic acid, and covalently linking nucleotides to the primer such that the added nucleotides are complementary to the template nucleic acid. Primer extension is ordinarily performed using an enzyme such as a DNA polymerase. Using appropriate buffers, pH, salts and nucleotide triphosphates, a template dependant polymerase such a DNA polymerase I (or the Klenow fragment thereof), taq or rTth polymerase XL incorporates a nucleotide complementary to the template strand on the 3' end of a primer which is hybridized to the template.

An "amplification primer" is a nucleic acid primer used for primer extension in a PCR reaction.

A "region" of a nucleic acid refers to the general area surrounding a structural feature of the nucleic acid, such as the termini of the molecule, an incorporated residue, or a specific subsequence.

A "restriction endonuclease cleavage site" denotes the site at which a known endonuclease cleaves DNA under defined environmental conditions.

A "restriction endonuclease recognition site" denotes the DNA site which is recognized by the endonuclease which brings about the cleavage reaction. The site is optionally from and restriction enzyme, including class I, class II, class IIS, class III, and class IV enzymes. Berger supra at chapter 11 describes several restriction enzymes. See also, Sambrook and Ausubel, both supra. The recognition site is distinct from the cleavage site for some enzymes, such as HphI and Bsg1.

An "antibody" is a polypeptide substantially encoded by an immunoglobulin gene or immunoglobulin genes, or fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplar immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist e.g., as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region thereby converting the $F(ab)'_2$ dimer into an Fab' monomer. The Fab' monomer is essentially an Fab with part of the hinge region (see, *Fundamental Immunology*, Third Edition, W. E. Paul, ed., Raven Press, N.Y. (1993), which is incorporated herein by reference, for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies. Immunoglobulins generated using recombinant expression libraries are also antibodies for purposes of this invention. Many antibodies are available, and methods of making antibodies are well known. See, Paul, id. and, e.g., Coligan (1991) *Current Protocols in Immunology* Wiley/Greene, NY; and Harlow and Lane (1989) *Antibodies: A Laboratory Manual* Cold Spring Harbor Press, NY).

A "molecular beacon" is an oligonucleotide to which is attached a fluorescent moiety and a quenching moiety. When the fluorescent moiety and the quenching moiety are in close proximity, no fluorescent signal is emitted. However, when the quenching moiety and the fluorescent moiety are no longer in close proximity, quenching does not occur and a fluorescent signal is emitted. Thus, cleavage of the oligonucleotide, for example, causes emission of a fluorescent signal.

DETAILED DESCRIPTION

The invention provides methods for studying interactions between molecules in vitro or in vivo. In one group of embodiments, the methods are useful for determining the positions of a protein on either DNA or RNA. These methods are referred to generally as "PINPOINT" methods. In other embodiments, the invention provides methods of detecting interactions between two molecules with high resolution and sensitivity. These methods, are referred to generally as "FLASHPOINT" methods.

PINPOINT Methods

In pinpoint methods, a target nucleic acid binding site is cleaved in a cell with a chimeric guide-endonuclease fusion molecule. In general, this involves providing a cell having the target nucleic acid and a chimeric guide molecule-endonuclease fusion molecule and permitting the fusion molecule to cleave the target nucleic acid, thereby producing a cleaved target nucleic acid with a site of cleavage. The target nucleic acid can be native to the cell, or introduced into the cell, e.g., by cellular transduction with the target nucleic acid. The chimeric guide endonuclease molecule is provided by transducing the cell with a nucleic acid encoding the molecule and expressing the molecule, or by delivering the molecule directly to the cell, i.e., by receptor-mediated uptake of the molecule, by liposomal delivery, or the like.

Uses of PINPOINT Methods

PINPOINT methods are useful for a number of different purposes. PINPOINT methods are used to identify genes involved in any disease state, including, inter alia, cancer, infection, Alzheimer's disease, atherosclerosis, AIDS and the like. PINPOINT methods are also suitable for studying basic questions regarding gene regulation, cell cycle regulation, DNA replication and DNA rearrangement. As described herein, methods are provided for monitoring nucleic acid-protein interactions in vivo.

A brief outline of some of the applications for PINPOINT methods is provided below; one of skill will immediately recognize many other uses for PINPOINT methods upon viewing this disclosure.

1. Pinpoint Methods Provide Basic Laboratory Research Tools. Many important events in the life of a cell or an organism occur on or near the DNA and RNA: transcription, DNA replication, repair, DNA modifications such as methylation, DNA rearrangement, attachment or positioning relative to nuclear structures such as the nuclear matrix or lamin, posttranscriptional modification of RNA, transport of RNA, attachment or positioning relative to cellular structures, sequestration and translation and cell cycle regulation. PINPOINT methods are applied to study all of these events in vivo. Although a number of protein-nucleic acids interactions have been studied in vitro, this does not accurately duplicate the environment that exists in a living cell and therefore misleads or leaves out important molecular events that occur in vivo. Furthermore, interactions of proteins not directly bound to DNA or RNA but positioned near DNA or RNA through protein-protein interaction can be studied. In addition, PINPOINT methods allow the visualization of protein complex nucleic acid interactions that are difficult to study where there are insufficient amounts of the purified protein complex. With PINPOINT, a pointer is incorporated into the complex and positioned by the cellular machinery on DNA or RNA, removing the need for protein purification. We found that electroshocking cells in the presence of calcium activated expressed chimeric proteins comprising MNase activity without killing cells. It is possible to cleave a particular DNA or RNA sequence by targeting a pointer having MNase activity to that site and activating MNase with calcium.

2. Pinpoint Methods Provide Basic Medical Research Tools. A number of diseases result from defective regulation of gene expression either at the transcriptional or translational level. Genes for proteins playing important roles in these diseases have been cloned but their targets on DNA or RNA are not completely known. For example, only a few genes directly regulated by the tumor suppressor protein p53 are known. By using PINPOINT methods, the remaining targets (and regulators) of p53 can be determined. By knowing the position of p53 in the genome, the functions of p53 can be determined. Understanding how p53 suppresses tumor growth is an important step in developing treatments for cancer. In a similar way, PINPOINT methods enhance the understanding of, diagnosis of and treatment of many diseases.

3. Genome Project. In several years, all of the human genome will be sequenced. The yeast Saccharomyces cerevisiae genome has been completely sequenced. Using point directory methods described herein, a map of all genomic positions for a protein of interest can be created for any given moment during the life cycle of a cell. Such genome wide pictures of protein-DNA/RNA interaction or protein-protein interaction will reveal important information on gene expression and cellular structures, including active promoter positions throughout the genome. In humans, knowledge of a DNA sequence for a gene by itself cannot identify the site of a promoter for the gene. However, by determining the genomic positions of protein bound to the promoter of all transcribed genes, one can determine the positions of all the active promoters in a given cell. In addition to the tools provided for basic research, the ability to accurately monitor promoter activity for many genes simultaneously aids in diagnosis of any disease state associated with gene misregulation, including all forms of cancer.

4. Clinical Tools. The repertoire of genes being transcribed or translated at any given moment reflects the diseased state of an abnormal cell. By determining the positions of RNA polymerase in the cell, one can determine what genes are transcribed in the cell; by determining the positions of the translation proteins such as ribosomes or EIF-4, one can determine what RNAs are being translated. Misplacement of a protein in the genome can lead a cell to a diseased state; therefore, determining genomic positions of crucial proteins can also aid in diagnostic methods.

5. Drug Screening Assays. Because the effects of potential modulators on protein-nucleic acids can be measured, a variety of very powerful screening assays for drugs are provided. The ability to screen rapidly for agents which modulate direct or indirect protein-nucleic acid interactions is of immediate value to the pharmaceutical industry.

Endonuclease Molecules

Micrococcal endonuclease produces a 3' phosphate and a 5' hydroxyl at the site of cleavage. Thus, guide fusion proteins of the invention which produce this activity are provided. Other guide fusions, such as Fok I (or other class IIS restriction endonuclease) fusions, produce a 5' phosphate and a 3' hydroxyl at the cleavage site. In either case, the cleaved target is treated in any of a variety of ways to facilitate amplification and/or detection of the target nucleic acid. Commonly, oligonucleotides are ligated to the cleaved target nucleic acid, or a terminal transferase enzyme is used to provide the cleaved target with defined ends for purification, subsequent PCR amplification and/or cloning.

In one embodiment, a first double-stranded target DNA and, optionally, a second double-stranded target DNA which correspond to each side of the cleavage site are made. A variety of techniques can be utilized to make the double-stranded nucleic acid, including oligo ligation, terminal transferase extension, enzymatic cleavage or ligation, PCR using primers to known sequences in the vicinity of the target, and the like. In one embodiment, a purification oligonucleotide comprising a class IIS restriction site is ligated to the first and/or second double-stranded target DNA, thereby producing a ligated target DNA. The purification oligonucleotide optionally further includes sequences for subsequent purification, cloning or PCR reactions, such as a class I restriction site, a region which hybridizes to a PCR primer and/or to a sequencing primer, a restriction site for cloning, a detectable label (e.g., biotin or avidin), or the like. The double stranded ligated target DNAs are cleaved with the class IIS restriction enzymes, producing target DNAs with termini that can be used in subsequent purification, cloning, or the like. The target DNAs with termini are isolated, typically by capture of the oligonucleotides which were ligated to the target DNAs. In one embodiment, the captured target DNAs are released by cleavage with a restriction enzyme which recognizes a site in the first and, optionally, the second ligated target DNAs, optionally by capture of the first and second detectable label and cleavage of the captured label with the first and second class I restriction enzyme. Optionally, the ligated target DNAs are ligated to form a ligated target site, which is optionally concatemerized for subsequent cloning and sequencing.

In embodiments in which a 3' phosphate is produced in cleavage by the guide-endonuclease fusion molecule, one of a variety of techniques are used for detection, isolation and/or amplification of the target nucleic acid. Typically, the 3' phosphate is dephosphorylated at the site of cleavage, thereby producing a 3' dephosphorylated cleavage end. This cleavage end is extended (e.g., by oligo ligation, or terminal transferase extension) and the 3' end is typically amplified, e.g., by PCR.

In certain embodiments, the target nucleic acid is a plasmid. In one class of embodiments, where the endonuclease domain of the chimeric molecule is a calcium inducible fusion partner such as micrococcal nuclease, the cell is permeabilized and treated with calcium to induce the calcium inducible chimeric molecule, which cleaves a single strand of the plasmid, leaving a 3' phosphate and a 5' hydroxyl at the site of cleavage. Plasmid nucleic acids are isolated from the cell, including the cleaved plasmid, thereby producing isolated plasmid nucleic acids. The cleaved plasmid is primer extended using a primer extension primer which is complementary to a strand of the plasmid comprising the cleavage site, thereby producing a double-stranded blunt end at the site of cleavage. A trapping oligonucleotide is ligated to the double-stranded blunt end, and the cleaved plasmid is PCR amplified using a PCR reaction mixture comprising an oligonucleotide which hybridizes to the trapping oligonucleotide, and, optionally, the primer extension primer, thereby amplifying the nucleic acid.

The 3' end can be dephosphorylated, thereby producing a 3' dephosphorylated cleavage end, which can be extended, e.g., by ligating an oligonucleotide to the end, or by treating the end with a terminal transferase enzyme. In many embodiments, the resulting extended 3' end is amplified and/or detected. Optionally, an internal PCR primer is used to prime PCR for amplification of the extended end.

In certain embodiments, cleavage of the target nucleic acid by the guide molecule-endonuclease chimera produces a 3' phosphate and a 5' hydroxyl at the site of cleavage. Typical processing steps performed on the cleaved nucleic acid include: 5' phosphorylating the cleaved nucleic acid at the site of cleavage to produce a 5' phosphorylated site; 3' dephosphorylating the cleaved nucleic acid at the site of cleavage; extending the 3' end of the cleavage site with a terminal transferase enzyme; extending the 3' end of the cleavage site by ligating a 3' extension oligonucleotide to the cleaved nucleic acid; primer extending the cleaved target nucleic acid using a primer extension primer which is complementary to a strand of the nucleic acid comprising the cleavage site, thereby producing a double-stranded blunt end at the site of cleavage; extending the 5' end by ligating a 5' extension oligonucleotide to the cleaved target DNA; PCR amplifying target nucleic acid using a primer complementary to the 5' extension oligonucleotide; and, performing nested PCR on amplified nucleic acids. Any or all of these steps are optionally practiced in the methods of the invention.

In one class of embodiments, the target nucleic acid is a genomic DNA and the chimeric molecule is calcium inducible. Optionally in this class, a cell is co-transfected with a marker vector and a chimeric nucleic acid vector encoding the chimeric guide molecule. The cell is cultured under conditions which permit expression of a marker encoded by the marker vector and the chimeric guide molecule, thereby producing a marked cell which expresses the marker and the chimeric guide molecule. The marked cell is typically isolated (i.e., by tracking the marker), thereby providing an isolated cell. The isolated cell is permeabilized with a mild detergent and treated with calcium, thereby inducing the calcium inducible chimeric molecule, which cleaves at least one strand of the target nucleic acid.

Optionally, where the chimeric molecule leaves a 3' phosphate and a 5' hydroxyl at the site of cleavage on the target nucleic acid, the 5' hydroxyl is phosphorylated, providing a 5' phosphate site on the cleaved nucleic acid for primer extension, oligo ligation, or other processing steps which aid in amplifying, purifying, cloning or detecting the cleaved target. For example, a trapping oligonucleotide is ligated to the 5' phosphate site to produce a target-linker nucleic acid. This trapping oligonucleotide is used as a molecular tag to amplify and/or purify the target-linker nucleic acid. Optionally, the site of cleavage is also or separately 3' dephosphorylated at the site of cleavage. This is performed separate from or in parallel with the 5' phosphorylation of the 5' hydroxyl. The 3' end is extended using a terminal transferase enzyme to produce an extended-target nucleic acid, or the 3' end is extended by ligation of an oligonucleotide. In either case, the extended-target nucleic acid is optionally PCR amplified to produce an amplified target-linker nucleic acid. Optionally, the 3' end of the resulting amplified target nucleic acid is extended using oligo ligation or terminal transferase, and again PCR amplified or detected.

In one embodiment, the cleavage site is detected by PCR. For example, PCR primers bracketing the cleavage site are used to prime a PCR reaction. If the target site is cleaved, the nucleic acid is not exponentially amplified by PCR. In a variation, determining the percentage cleaved is performed by this method using standard quantitative PCR methods. See, PCR Protocols A Guide to Methods and Applications (Innis et al. eds) Academic Press Inc. San Diego, Calif. (1990) (Innis).

In one class of embodiments, the target nucleic acid is an RNA. In certain embodiments, cleavage of the RNA by the guide molecule-endonuclease chimera produces a 3' phosphate and a 5' hydroxyl at the site of cleavage. Typically, RNA is isolated from the cell, thereby producing isolated RNA. Optionally, an RNA terminator is coupled to 3' hydroxyls present in the isolated RNA, to block subsequent amplification of RNAs other than the target RNA. Typically, the 3' phosphate is dephosphorylated with a kinase enzyme or a phosphatase enzyme to produce a dephosphorylated target RNA. Optionally, an oligonucleotide is ligated to the dephosphorylated target RNA. In one embodiment, the oligonucleotide comprises a binding site for a class IIS restriction enzyme, which can be used in subsequent purification steps.

Typically, the cleaved target RNA is reverse transcribed for further processing, optionally using a reverse transcription primer which hybridizes to an oligonucleotide ligated to the RNA to prime the reverse transcription reaction, thereby producing a reverse transcribed nucleic acid. Generally, the resulting reverse transcribed RNA-DNA hybrid nucleic acid is treated with an enzyme with RNAse H activity, and a second enzyme with DNA polymerase activity to convert the hybrid into a double-stranded target DNA.

The double-stranded target DNA can be cleaved with a restriction enzyme, thereby producing a restricted target DNA. Ligation of an oligonucleotide to the restricted target DNA facilitates further purification, amplification, cloning or sequencing of the restricted target DNA.

Typical processing steps for treating cleaved target nucleic acids of the invention can include one or more of: random primer extending the cleaved target nucleic acid, ligating a blocking oligonucleotide to the cleaved target nucleic acid 5' phosphorylating the cleaved target nucleic acid, cleaving the target nucleic acid with a restriction enzyme, cleaving an amplified target nucleic acid with a restriction enzyme, trapping cleaved target DNA to produce trapped target DNA, ligating a reaching oligonucleotide to the trapped target DNA, amplifying the target DNA using PCR, blocking a 3'OH terminal of the cleaved target nucleic acid with a terminal transferase, blocking a 3'OH terminal of the cleaved target nucleic acid with a blocking oligonucleotide, 3' dephosphorylating the cleaved target nucleic acid, 3' end extending the cleaved target nucleic acid with a terminal transferase enzyme, 3' end extending the cleaved target nucleic acid by ligating an oligonucleotide onto the 3' end of a cleaved target nucleic acid, primer extending the cleaved target nucleic acid, cloning the guide molecule-chimera, or a combination of any of these steps.

Transducing Cells and Detecting Cleavage Products for PINPOINT Methods

In one class of embodiments, methods of cleaving a target nucleic acid binding site in a cell with a chimeric guide-endonuclease fusion molecule are provided. Typically, a cell having the target nucleic acid and a chimeric nucleic acid encoding the chimeric guide molecule-endonuclease fusion molecule is provided, the nucleic acids are expressed and the resulting fusion molecule cleaves the target nucleic acid.

In certain embodiments, the guide molecule-chimera is cloned and expressed in the cell. In other embodiments, the fusion molecule is delivered to the cell (e.g., by liposome delivery, receptor mediated uptake or the like). Optionally, the cell is provided by transducing the cell with either the target nucleic acid or the guide-endonuclease, or both. The cell optionally comprises further components such as a reporter gene, a selectable marker, a label, specific genomic mutations, or the like.

The cleaved target nucleic acid is optionally amplified, and/or detected. The cleaved target is optionally cloned, and/or sequenced, and is optionally subjected to one of a variety of further processing steps, as described herein. Detection methods include nested PCR, Southern blotting, northern blotting, and cloning and sequencing the target nucleic acid.

Transduction of cells with a target nucleic acids, nucleic acids encoding a chimeric guide-endonuclease fusion molecule, marker genes, or the like, is performed using standard methods. Host cells are competent or rendered competent for transformation by various means. There are several well-known methods of introducing DNA or other materials (e.g., chimeric guide-endonuclease fusion molecules) into cells. These include calcium phosphate precipitation, fusion of the recipient cells with bacterial protoplasts containing the DNA, treatment of the recipient cells with liposomes containing the DNA, DEAE dextran, receptor-mediated endocytosis, electroporation and microinjection of the DNA directly into the cells. Electroporation is a preferred method when a nucleic acid is to be transduced into the cell. Examples of appropriate cloning and transduction techniques, as well as related techniques directed to detecting and assessing nucleic acids by sequencing, Southern analysis, northern analysis and the like are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1996 Supplement) (Ausubel).

As discussed, receptor-mediated endocytosis provides an efficient means of causing a cell to ingest material which binds to a cell surface receptor. See, Wu and Wu (1987) *J. Biol. Chem.* 262:4429–4432; Wagner et al. (1990) *Proc. Natl. Acad. Sci. USA* 87:3410–3414, and EP-A1 0388 758. To cause a cell to ingest a nucleic acid or a chimeric molecule, the chimeric molecule or nucleic acid is complexed to material recognized by a cellular receptor. For example, naked plasmid DNA bound electrostatically to poly-1-lysine or poly-1-lysine-transferrin which is linked to defective adenovirus mutants can be delivered to cells with transfection efficiencies approaching 90% (Curiel et al. (1991) *Proc Natl Acad Sci USA* 88:8850–8854; Cotten et al. (1992) *Proc Natl Acad Sci USA* 89:6094–6098; Curiel et al. (1992) *Hum Gene Ther* 3:147–154; Wagner et al. (1992) *Proc Natl Acad Sci USA* 89:6099–6103; Michael et al. (1993) *J Biol Chem* 268:6866–6869; Curiel et al. (1992) *Am J Respir Cell Mol Biol* 6:247–252, and Harris et al. (1993) *Am J Respir Cell Mol Biol* 9:441–447). The adenovirus-poly-1-lysine-DNA conjugate binds to the normal adenovirus receptor and is subsequently internalized by receptor-mediated endocytosis.

Suitable methods for the detection of cleaved target nucleic acids in biological samples include Southern analysis, PCR, northern analysis, in situ hybridization (including fluorescent in situ hybridization (FISH), reverse chromosome painting, FISH on DAPI stained chromosomes, generation of Alphoid DNA probes for FISH using PCR, PRINS labeling of DNA, free chromatin mapping and a variety of other techniques described in Tijssen (1993) *Laboratory Techniques in biochemistry and molecular biology—hybridization with nucleic acid probes parts I and II*, Elsevier, N.Y., and, Choo (ed) (1994) *Methods In Molecular Biology* Volume 33—*In Situ Hybridization Protocols*, Humana Press Inc., New Jersey (see also, other books in the Methods in Molecular Biology series)). PCR is a preferred amplification and detection method for amplifying and detecting cleaved target nucleic acids.

A variety of automated solid-phase detection techniques are also appropriate. For instance, very large scale immobilized polymer arrays (VLSIPS™), available from Affymetrix, Inc. in Santa Clara, Calif. are used for the detection of nucleic acids. See, Tijssen (supra.), Fodor et al. (1991) *Science*, 251: 767–777; Sheldon et al. (1993) *Clinical Chemistry* 39(4): 718–719, and Kozal et al. (1996) *Nature Medicine* 2(7): 753–759. In one embodiment, the invention provides methods of detecting target nucleic acids, in which target nucleic acids, or amplified nucleic acids corresponding to target nucleic acids, are hybridized to an array of nucleic acids. For example, in the pinpoint address methods described supra, oligonucleotides which hybridize to all possible PINPOINT address sequences are optionally synthesized on a DNA chip (such chips are available from Affymetrix) and the PINPOINT address fragments are hybridized to the chip for simultaneous analysis of multiple target nucleic acids, or multiple amplified target nucleic acids. The target nucleic acids that are present in the sample which is assayed are detected at specific positions on the chip.

Methods of culturing cells transduced with target nucleic acids, nucleic acids encoding chimeric guide-endonuclease fusion proteins, marker nucleic acids and the like are known, and are taught in Berger, Sambrook and Ausubel, all supra, as well as Freshney (*Culture of Animal Cells, a Manual of Basic Technique, third edition* Wiley-Liss, New York (1994)) and the references cited therein. See, also, Kuchler et al. (1977) *Biochemical Methods in Cell Culture and Virology*, Kuchler, R. J., Dowden, Hutchinson and Ross, Inc. PINPOINT methods are applied to essentially any cell system available, including bacterial cells, insect cells, plant cells, yeast cells, fungal cells and the like by expressing or delivering the chimeric guide endonuclease molecule to the cell. Similarly, a transgenic organism expressing the chimeric guide endonuclease molecule can be made using available techniques. Techniques for making transgenic plants, insects and vertebrates (including mammals) are well known and can be applied to the present invention.

Modification of the Cleaved Target Nucleic Acid

In some embodiments, cleavage of the target nucleic acid by the chimeric guide-endonuclease fusion molecule leaves a 5' P and a 3' OH at the site of cleavage. In these embodiments, the ends are optionally treated by ligation of an oligonucleotide, or extension by a terminal transferase to leave a molecular "tag" to which subsequent PCR primer oligonucleotides and/or detection oligonucleotides are hybridized in subsequent amplification and/or detection strategies.

In other embodiments, cleavage by the chimeric guide-endonuclease fusion molecule leaves a 3' P and a 5' OH terminus. For example, cleavage by a micrococcal endonuclease domain leaves 3' P and a 5' OH termini at the cleavage site. Targets with these termini are amplified and/or isolated by taking advantage of these unique termini. For example, background in subsequent amplification steps is reduced by ligating a blocking reagent such as an oligonucleotide or oligonucleotide analogue onto all available termini in a sample following the cleavage reaction. A ligase enzymes which does not ligate an oligonucleotide to the 3' P or the 5' OH is used, resulting in all of the termini which are unrelated to the target cleavage site being marked by the blocking reagent which blocks subsequent ligation to the unrelated termini. For example, in RNA PINPOINT strategies where 3' P and 5' OH ends are made with the chimeric molecule, any regular 3' OH ends in the RNA mixture are first blocked with T4 RNA ligase and a terminating ribose nucleotide such as a 3'-O-methylguanosine 5' triphosphate. This prevents unwanted ligation of oligonucleotides to the RNA in subsequent amplification, purification or reverse transcription protocols.

Subsequently, the sample is treated with a kinase or phosphatase enzyme as appropriate to convert the 5' OH to a 5' P, and the 3' P to a 3' OH. The cleavage sites then have an oligonucleotide ligated which permits subsequent processing. Ligase, phosphatase, kinase and terminal transferase enzymes are widely available from a variety of commercial sources known to one of skill. Sambrook, Ausubel, Berger and Innis, all supra, provide appropriate reaction conditions for these enzymes, as do commercial suppliers of the enzymes.

Oligonucleotide Ligation to Reaction Cleavage Products

In the methods of the invention, a chimeric guide-endonuclease fusion molecule is used to cleave a target nucleic acid. The cleavage site produced by this cleavage reaction provide cleavage ends which are conveniently used for attaching molecular tags such as oligonucleotides, which are used in subsequent steps for purification, amplification and/or detection of the target nucleic acid.

Oligonucleotides are typically synthesized chemically according to the solid phase phosphoramidite triester method described by Beaucage and Caruthers (1981), *Tetrahedron Letts.*, 22(20):1859–1862, e.g., using an automated synthesizer, as described in Needham-VanDevanter et al. (1984) *Nucleic Acids Res.*, 12:6159–6168. Oligonucleotides can also be custom made and/or ordered from a variety of commercial sources known to persons of skill, or produced recombinantly. Purification of oligonucleotides, where necessary, is optionally performed by native acrylamide gel electrophoresis or by anion-exchange HPLC as described in Pearson and Regnier (1983) *J. Chrom.* 255:137–149, or by various chromatographic methods known to persons of skill. A variety of specialized devices are commercially available for oligonucleotide purification. The sequence of oligonucleotides can be verified using the chemical degradation method of Maxam and Gilbert (1980) in Grossman and Moldave (eds.) Academic Press, New York, *Methods in Enzymology* 65:499–560. Ligation of oligonucleotides to a cleavage site is performed using a ligase enzyme, as described in Sambrook, Berger and Ausubel, all supra, or chemically ligated using standard organic coupling reactions as described in March (*Advanced Organic Chemistry Reactions, Mechanisms and Structure* 4th ed J. Wiley and Sons (New York, 1992), and the references cited therein.

In an alternative embodiment, a terminal transferase enzyme is used to synthesize a chain of nucleotides on a cleavage site. Typically, a nucleotide with a selected polynucleotide sequence is produced, such as a poly-G sequence. This added sequence can act as a molecular tag for subsequent processing steps in the same way as a ligated oligonucleotide.

As described, in certain embodiments, unusual cleavage ends are produced, leaving a 3' phosphate and a 5' OH. To make these ends suitable for ligation or terminal transferase addition, the site is treated with a kinase (e.g., $T_4$ kinase) or phosphatase (calf alkaline phosphatase) enzyme to add or delete a phosphate from the site as needed. Where ligation of an oligonucleotide to an RNA is desired, a $T_4$ RNA ligase or similar enzyme can be used to ligate the oligonucleotide to the RNA.

In certain embodiments, an oligonucleotide or nucleic acid corresponding to the target nucleic acid comprises a detectable label. Detectable labels are compositions detectable by spectroscopic, photochemical, biochemical, immunochemical, or chemical means. For example, useful labels include $^{32}P$, $^{33}P$, fluorescent dyes, electron-dense reagents, enzymes (e.g., as commonly used in an ELISA), biotin, dioxigenin, or haptens and proteins for which antisera or monoclonal antibodies are available. In certain embodiments, particularly where the target nucleic acid is a genomic or other relatively rare nucleic acid, the label is used in subsequent processing steps to partially purify a target nucleic acid having an oligonucleotide label. This is typically done by affinity chromatography using a cognate ligand to the label, or by isolating the nucleic acid on beads having a cognate ligand to the label, or the like.

PCR of Cleaved Target DNA

A variety of procedures for PCR amplifying cleaved oligonucleotides are provided herein, and other in vitro amplification methods are also useful for amplifying a target nucleic acid. In vitro amplification techniques suitable for amplifying sequences to provide a large nucleic acid or for subsequent analysis, sequencing or subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of amplifying large nucleic acids are summarized in Cheng et al. (1994) *Nature* 369: 684–685 and the references therein. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

One of skill will appreciate that two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. An extensive guide to the hybridization of nucleic acids is found in Tijssen (1993) *Laboratory Techniques in Biochemistry and Molecular Biology—Hybridization with Nucleic Acid Probes* part I chapter 2 "overview of principles of hybridization and the strategy of nucleic acid probe assays", Elsevier, N.Y.

In the context of the present invention, it is common to hybridize a primer to a template nucleic acid for primer extension, or during PCR. Appropriate solutions and temperatures for hybridization are sequence dependent, with the selection of appropriate hybridization conditions being routine. See, Tijssen et al., id. Generally, highly stringent hybridization conditions are selected to be about 5–10° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. See also, Innis, supra.

While many sequences can be used to construct primers, selecting optimal amplification primers is optionally done using computer assisted consideration of available sequence and excluding potential primers which do not have desired hybridization characteristics, and/or including potential primers which meet selected hybridization characteristics. This is done by determining all possible nucleic acid primers, or a subset of all possible primers with selected hybridization properties (e.g., those with a selected length and G:C ratio) based upon the known sequence. The selection of the hybridization properties of the primer is dependent on the desired hybridization and discrimination properties primer. In general, the longer the primer, the higher the melting temperature. However, longer primers are not as specific because a single mismatch has less of a destabilizing effect on hybridization than a single mismatch on a short nucleic acid duplex; thus, long primers can create unwanted PCR products. It is expected that one of skill is thoroughly familiar with the theory and practice of nucleic acid hybridization and primer selection. Gait, ed. *Oligonucleotide Synthesis: A Practical Approach*, IRL Press, Oxford (1984); W. H. A. Kuijpers *Nucleic Acids Research* 18(17), 5197 (1994); K. L. Dueholm *J. Org. Chem.* 59, 5767–5773 (1994); S. Agrawal (ed.) *Methods in Molecular Biology*, volume 20; and Tijssen (1993) *Laboratory Techniques in biochemistry and molecular biology—hybridization with nucleic acid probes*, e.g., part I chapter 2 "overview of principles of hybridization and the strategy of nucleic acid probe assays", Elsevier, N.Y. provide a basic guide to nucleic acid hybridization. Innis supra provides an overview of primer selection.

Most typically, amplification primers are between 8 and 100 nucleotides in length, and preferably between about 10 and 30 nucleotides in length. Most preferably, the primers are between 15 and 45 nucleic acids in length. For example, in one preferred embodiment, the nucleic acid primers are about 17–30 nucleotides in length.

One of skill will recognize that the 3' end of an amplification primer is more relevant in PCR than the 5' end. Investigators have reported PCR products where only a few nucleotides at the 3' end of an amplification primer were complementary to a DNA to be amplified. In this regard, nucleotides at the 5' end of a primer can incorporate structural features unrelated to the target nucleic acid; for instance, in one preferred embodiment, a second primer hybridization site (or a complement to such as primer, depending on the application) is incorporated into any amplification primer. For example, an amplification primer derived from a sequencing primer used in a standard sequencing kit, such as one using a biotinylated or dye-labeled universal M13 or SP6 primer can be incorporated into an amplification primer. Similarly, restriction endonuclease recognition sites are optionally incorporated in a similar manner.

In some embodiments, amplification oligonucleotide sequences are selected to hybridize only to a perfectly complementary DNA, with the nearest mismatch hybridization possibility from a DNA sequence unrelated to the target nucleic acid which is known to exist in a cell having at least about 50 to 70% hybridization mismatches, and preferably 100% mismatches for the terminal 5 nucleotides at the 3' end of the primer.

The amplification primers are optionally selected so that no secondary structure forms within the primer. Self-complementary primers have poor hybridization properties, because the complementary portions of the primers self hybridize (i.e., form hairpin structures). The primers are also selected so that the primers do not hybridize to each other, thereby preventing duplex formation of the primers in solution, and possible concatenation and unwanted amplification of the primers during PCR.

Where sets of amplification primers (i.e., the 5' and 3' primers used for exponential amplification) are of a single length, the primers are optionally selected so that they have roughly the same, and preferably exactly the same overall base composition (i.e., the same A+T to G+C ratio of nucleic acids). Where the primers are of differing lengths, the A+T to G+C ratio is determined by selecting a thermal melting temperature for the primer-DNA hybridization, and selecting an A+T to G+C ratio and probe length for each primer which has approximately the selected thermal melting temperature.

One of skill will recognize that there are a variety of possible ways of performing the above selection steps, and that variations on the steps are appropriate. Most typically, selection steps are performed using simple computer programs to perform the selection as outlined above; however, all of the steps are optionally performed manually. One available computer program for primer selection is the MacVectorm program from Kodak. In addition to commercially available programs for primer selection, one of skill can easily design simple programs for any of the preferred amplification steps.

Screening for In Vivo Binding Sites

The present invention provides methods of screening test nucleic acids for in vivo binding sites which are cleaved by a chimeric guide molecule. Typically, a cell comprising a chimeric nucleic acid encoding the chimeric guide molecule and a test nucleic acid is provided, the chimeric nucleic acid is expressed in the cell, thereby producing chimeric guide molecule in the cell and, the cell is incubated under conditions in which the guide molecule is active. If the chimeric guide molecule cleaves the test nucleic acid, the test nucleic acid comprises an in vivo binding site for the chimeric guide molecule. The ability to test whether a particular chimeric molecule cleaves a target site provides evidence for whether a naturally occurring molecule corresponding to the guide domain binds the target in vivo. This, in turn, is of value for basic research, for finding targets for therapeutic genes, for targeting therapeutics to disease-related genes, or the like. For example, if a guide domain corresponding to a tumor suppressor is found to interact with a target site in the promoter of a gene which mediates disease, then therapeutics which modulate the activity of the tumor suppressor can be tested for an effect on the gene which mediates disease.

In one assay of the invention, the test nucleic acid encodes a promoter sequence operably linked to a reporter gene. Detection of the presence or absence of reporter gene expression is an indicator for whether the test nucleic acid comprises an in vivo binding site for the chimeric guide molecule. A variety of reporter gene plasmid systems are known, such as the common chloramphenicol acetyltransferase (CAT) and beta-galactosidase (e.g., bacterial LacZ gene) reporter systems, the firefly luciferase gene (See, e.g., Cara et al., (1996) *J. Biol. Chem.*, 271: 5393–5397), the green fluorescence protein (see, e.g., Chalfie et al. (1994) *Science* 263:802) and many others. Selectable markers which facilitate cloning of the vectors of the invention are optionally included. Sambrook and Ausubel, both supra, provide an overview of selectable markers.

Promoters selected as targets for testing in conjunction with a reporter gene can be from essentially any gene. Preferred promoters direct expression of pathogen or disease related genes, such as a viral promoter (HIV-1 or HIV-2 LTRs, HTLV-LTRs, Herpes virus tk promoter, a vaccinia promoter, a pox virus promoter, a flu virus promoter, an adenovirus promoter, etc.), an oncogene promoter (e.g., a promoter from p53, c-myc, fos, etc.), or the like.

Parallel Screening Formats

In one class of embodiments, the cell is provided by co-transducing the cell with a plasmid encoding the target nucleic acid and a plasmid encoding the chimeric guide molecule. Optionally, one or more additional plasmids comprising one or more additional test nucleic acids are also transduced into the cell, and the effect of the chimeric guide molecule is assessed simultaneously on more than one test nucleic acid.

Parallel screening formats are provided, in which a second cell comprising a second chimeric nucleic acid encoding a second chimeric guide molecule and a second test nucleic acid is provided. The second chimeric nucleic acid is expressed and the effect of the chimeric nucleic acid on the second test nucleic acid is monitored. This parallel screening assay is suitable for automation, providing the ability to screen the activity of multiple chimeric guide molecules against multiple target nucleic acids in a single assay. The use of control nucleic acids, such as positive control nucleic acids which are known to be cleaved by a particular guide nucleic acid to verify that the cellular environment permits chimeric molecule activity, and negative control nucleic acids which are known to remain uncleaved in the presence of the chimeric molecule, are optionally used in the cells of the invention.

A number of cleavage reactions are optionally monitored simultaneously, e.g., using a format which permits simultaneous analysis of several samples (microtiter plates, etc.). In a preferred embodiment, the assays are automated, e.g., using robotics for pipetting samples into microtiter plates. For example, a Zymate XP (Zymark Corporation; Hopkinton, Mass.) automated robot using Microlab 2200 (Hamilton; Reno, Nev.) pipetting station can be used to transfer cell samples to a 96 well microtiter plate to set up several parallel simultaneous assays of cleavage activity of one or more chimeric molecule on one or more target nucleic acid.

The invention provides methods of detecting a nucleic acid binding molecule modulating agent. In the methods, a cell comprising a test nucleic acid binding site (e.g., a promoter sequence which is bound by a transcription factor) and a chimeric guide-endonuclease molecule is provided. The cell is contacted with the potential modulating agent, and the rate of cleavage of the test nucleic acid binding site by the chimeric nucleic acid binding molecule in the presence of the agent in measured. Typically, this measurement is compared to the rate of cleavage of the test nucleic acid in the absence of the modulating agent. If the cleavage rate is increased or decreased, the potential modulator is confirmed to be a modulating agent. To verify that the modulation is due to effects on the guide domain, and not on the endonuclease domain, the modulator is tested for modulatory activity against a second chimeric guide molecule which has the same endonuclease domain as the chimeric molecule first tested. Modulators which do not affect the activity of second chimeric molecule are specific for the guide domain of the chimeric molecule first tested. Multiple assays are preferably performed in parallel in the methods of the invention, with several agents and/or several activities being screened simultaneously (e.g., in a microtiter format as described), a decided advantage if large numbers of agents and/or target nucleic acids and/or chimeric molecules are to be screened.

Cleavage can be measured in any of a variety of ways, including quantitative PCR amplification of the cleavage products, assessment of a reporter gene construct having a promoter as the target nucleic acids as set forth above, by measuring incorporation of a radioactive nucleotide into amplification products, or the like. In an embodiment, the amount of product polynucleotide is determined by contacting an amplification reaction mixture, following a suitable incubation period, with a substrate which selectively immobilizes or binds to polynucleotides and which substantially does not immobilize or bind to mononucleotides or labelling reagents; one example of such a substrate is a charged membrane (e.g., a glass fiber filter such as the 2SC filter from Whatman, Nylon 66, nitrocellulose, DEAE paper, or the like). This format is conveniently combined with the microtiter format, e.g., using a unifilter plate (Whatman GF/C glass fiber filter bottom).

Alternatively, amplification products are chromatographed or electrophoresed (e.g., PAGE) to separate polynucleotide products from unincorporated nucleotides or other materials. In either case, product nucleic acids are optionally isolated and cloned, using techniques known in the art. See, Sambrook, Berger, Ausubel and Innis, all supra.

In one class of embodiments, the invention provides methods of cleaving target nucleic acids in vitro or in vivo. In the methods, a target nucleic acid is contacted by a guide-micrococcal endonuclease fusion molecule in the presence of calcium. The guide-micrococcal endonuclease fusion then cleaves the target nucleic acid. In one embodiment, the cleavage is performed in situ, e.g., in a tissue or cell sample on a solid substrate such as a microscope slide, an Affymetrix chip, or the like.

Chimeric Guide-Endonuclease Molecules

A variety of target nucleic acids are bound by the chimeric guide endonuclease fusion molecules of the invention, including genomic nucleic acids with known sequences of nucleotides, genomic nucleic acid with unknown sequences of nucleotides, plasmids with sequences of known nucleotides, plasmids with sequences of unknown nucleotides, RNA with sequences of known nucleotides, and RNA with unknown sequences of nucleotides. A variety of chimeric guide molecules are used for assessing the target nucleic acids, including those in which the guide domain is a DNA binding protein, an RNA binding protein, a protein which binds to a DNA binding protein, a protein which binds to an RNA binding protein, an antibody protein which binds to a DNA binding protein, a first antibody protein which binds to a second antibody protein, and an antibody protein which binds to an RNA binding protein. In one embodiment, the target nucleic acid is contacted with a primary antibody which binds to a DNA binding protein bound to the target nucleic acid. The chimeric guide-endonuclease fusion protein comprises a secondary antibody which binds to the primary antibody.

The guide domain can also be a molecule chemically conjugated to the endonuclease domain which binds to a target nucleic acid, or to a protein associated with the target nucleic acid, such as a guide nucleic acid, an antibody fusion or the like. Preferred endonuclease domains are inducible rather than constitutive, conferring the ability to regulate cleavage by the endonuclease domain. A preferred endonuclease is micrococcal nuclease, which is calcium inducible, and which cleaves both DNA and RNA. A particularly preferred endonuclease domain is a micrococcal nuclease domain with constitutive in vivo activity which is lower than the native micrococcal nuclease enzyme. This lower constitutive activity lowers background cleavage activity, increasing the signal to noise ratio in the methods of the invention.

Common guide domains include transcription factors (activators), silencers, nuclear receptors, general transcription machinery and modifiers of these factors, oncogenes (e.g., myc, jun, fos, myb, max, mad, rel, ets, bcl, myb, mos family members etc.), tumor promoters, metastasis and invasiveness promoters or suppressors and their associated factors and modifiers; tumor suppressors (e.g. p53, WT1, MDM2, Rb family) and their associated factors and modifiers; DNA repair enzymes and their associated factors and modifiers; DNA rearrangement enzymes and their associated factors and modifiers, cell cycle proteins and their associated factors and modifiers; chromatin associated proteins and their modifiers (e.g., kinases, acetylases and deacetylases); DNA modifying enzymes (e.g., methyltransferases, topoisomerases, helicases, ligases, kinases, phosphatases, polymerases) and their associated factors and modifiers; RNA modifying enzymes and their associated factors and modifiers, RNA binding factors (directly or indirectly) and their associated factors and modifiers, factors that control chromatin, DNA, RNA and RNP (ribonuclear protein) structure, movement and localization and their associated factors and modifiers; factors derived from microbes (e.g., prokaryotes, eukaryotes and virus) and factors that associate with or modify them.

While a complete protein can be used as a guide domain, portions of proteins that are capable of binding to nucleic acids, directly or indirectly, are also useful as guide domains. To identify such nucleic acid binding domains, one can perform assays such as an electrophoretic mobility shift assay (EMSA) (Scott et al. (1994) *J. Biol. Chem.* 269: 19848–19858), in which a nucleic acid sequence of interest is allowed to associate with various fragments of a molecule that is capable of binding to the nucleic acid sequence. Association of a portion of the protein with the nucleic acid will result in a retardation of the electrophoretic mobility of the nucleic acid. Another method by which one can identify nucleic acid binding moieties that are suitable for use as guide domains is DNase I footprinting.

Common polypeptides from which one can obtain a guide domain include polypeptides that are involved in transcription, both regulated and basal transcription. Such polypeptides include transcription factors and coactivators, silencers, nuclear receptors, general transcription machinery and modifiers of these factors. See, e.g., Goodrich et al., *Cell* 84: 825–30 (1996) for a review of proteins and nucleic acid elements involved in transcription. Transcription factors in general are reviewed in Barnes and Adcock, *Clin. Exp. Allergy* 25 Suppl. 2: 46–9 (1995) and Roeder, *Methods Enzymol.* 273: 165–71 (1996). Databases dedicated to transcription factors are known. See, e.g., Science 269:630. Intracellular receptor transcription factors are described in, for example, Rosen et al., *J. Med. Chem.* 38: 4855–74 (1995). The C/EBP family of transcription factors are reviewed in Wedel et al., *Immunobiology* 193: 171–85 (1995). Coactivators and co-repressors that mediate transcription regulation by nuclear hormone receptors are reviewed in, for example, Meier, *Eur. J Endocrinol.* 134(2): 158–9 (1996) and Kaiser et al., *Trends Biochem. Sci.* 21: 342–5 (1996). GATA transcription factors, which are involved in regulation of hematopoiesis, are described in, for example, Simon, *Nat. Genet.* 11: 9–11 (1995); Weiss et al., *Exp. Hematol.* 23: 99–107. TATA box binding protein (TBP) and its associated TAF polypeptides (which include TAF30, TAF55, TAF80, TAF110, TAF150, and TAF250) are described in Goodrich and Tjian, *Curr. Opin. Cell Biol.* 6: 403–9 (1994) and Hurley, *Curr. Opin. Struct. Biol.* 6: 69–75 (1996). The STAT family of transcription factors are reviewed in, for example, Barahmand-pour et al., *Curr. Top. Microbiol. Immunol.* 211: 121–8 (1996). Transcription factors involved in disease are reviewed in Aso et al ., *J. Clin. Invest.* 97: 1561–9 (1996).

Kinases, phosphatases, and other proteins that modify polypeptides involved in gene regulation are also useful as guide domains. Such modifiers are often involved in switching on or off transcription mediated by, for example, hormones. Kinases involved in transcription regulation are reviewed in Davis, *Mol. Reprod. Dev.* 42: 459–67 (1995), Jackson et al., *Adv. Second Messenger Phosphoprotein Res.* 28: 279–86 (1993), and Boulikas, *Crit. Rev. Eukaryot. Gene Expr.* 5: 1–77 (1995), while phosphatases are reviewed in, for example, Schonthal, *Semin. Cancer Biol.* 6: 239–48 (1995). Nuclear tyrosine kinases are described in Wang, *Trends Biochem. Sci.* 19: 373–6 (1994).

As described, guide domains can also be obtained from the gene products of oncogenes (e.g., myc, jun, fos, myb, max, mad, rel, ets, bcl, myb, mos family members, etc.) and tumor suppressors (e.g., p53, WT1, MDM2, Rb family, and the like) and their associated factors and modifiers. Oncogenes are described in, for example, Cooper, *Oncogenes*, 2nd ed., The Jones and Bartlett Series in Biology, Boston, Mass., Jones and Bartlett Publishers, 1995. The ets transcription factors are reviewed in Waslylk et al., *Eur. J. Biochem.* 211: 7–18 (1993) and Crepieux et al., *Crit. Rev. Oncog.* 5: 615–38 (1994). myc oncogenes are reviewed in, for example, Ryan et al., *Biochem. J.* 314: 713–21 (1996). The jun and fos transcription factors are described in, for example, *The Fos and Jun Families of Transcription Factors*, Angel PE, Herrlich Pa., eds. Boca Raton, Fla., CRC Press, 1994. The max oncogene is reviewed in Hurlin et al., *Cold Spring Harb. Symp. Quant. Biol.* 59: 109–16. The myb gene family is reviewed in Kanei-Ishii et al., *Curr. Top. Microbiol. Immunol.* 211: 89–98 (1996). The mos family is reviewed in Yew et al., *Curr. Opin. Genet. Dev.* 3: 19–25 (1993).

Tumor promoters, metastasis and invasiveness promoters or suppressors and their associated factors and modifiers are also suitable for use as guide domains. Proteins involved in carcinogenesis, including tumor suppressors and activators, are reviewed in Schmandt et al., *Clin. Chem.* 39 (11 Pt 2): 2375–85 (1993) and Kelley et al., *Adv. Intern. Med.* 39: 93–122 (1994). Tumor suppressors are reviewed in Hinds et al., *Curr. Opin. Genet. Dev.* 4: 135–41 (1994). The p53 tumor suppressor in particular is described in Hainaut, *Curr. Opin. Oncol.* 7: 76–82 (1995) and Cox and Lane, *Bioessays*, 17: 501–8 (1995), while the Rb family is reviewed in Sidle et al., *Crit. Rev. Biochem. Mol. Biol.* 31: 237–71 (1996). Invasiveness promoters and suppressors are reviewed in, for example, Mareel et al., *Mol. Biol. Rep.* 19: 45–67 (1994).

The chimeric endonucleases can also include a guide domain polypeptide that is obtained from DNA repair enzymes and their associated factors and modifiers. DNA repair systems are reviewed in, for example, Vos, *Curr. Opin. Cell Biol.* 4: 385–95 (1992); Sancar, *Ann. Rev. Genet.* 29: 69–105 (1995); Lehmann, *Genet. Eng.* 17: 1–19 (1995); and Wood, *Ann. Rev. Biochem.* 65: 135–67 (1996). DNA rearrangement enzymes and their associated factors and modifiers (see, e.g., Gangloff et al., *Experientia* 50: 261–9 (1994); Sadowski, *FASEB J.* 7: 760–7 (1993)), cell cycle proteins and their associated factors and modifiers are also useful as guide domains. For example, proteins involved in DNA replication can be used to construct chimeric endonucleases. DNA replication proteins are described in Kearsey et al., *Curr. Opin. Genet. Dev.* 6: 208–14 (1996) and Donovan et al., *Curr. Opin. Genet. Dev.* 6: 203–7 (1996). Cell cycle proteins are also described in Stein et al., *Int. J Obes. Relat. Metab. Disord.* 20 Suppl 3: S84–90 (1996).

Similarly, guide domain polypeptides can be derived from DNA modifying enzymes (e.g., methyltransferases, topoisomerases, helicases, ligases, kinases, phosphatases, polymerases) and their associated factors and modifiers. Helicases are reviewed in Matson et al., *Bioessays*, 16: 13–22 (1994), and methyltransferases are described in Cheng, *Curr. Opin. Struct. Biol.* 5: 4–10 (1995). Chromatin associated proteins and their modifiers (e.g., kinases, acetylases and deacetylases), such as histone deacylase (Wolffe, *Science* 272: 371–2 (1996)) are also useful as guide domains.

RNA modifying enzymes and their associated factors and modifiers, RNA binding factors (directly or indirectly) and their associated factors and modifiers are also useful as guide domains. For review of protein-RNA interactions, see, Draper, *Ann. Rev. Biochem.* 64: 593–620 (1995) and Burd et al., *Science* 29: 615–21 (1994). RNP domains are reviewed in Nagai et al., *Trends Biochem. Sci.* 20: 235–40 (1995).

Factors that control chromatin, DNA, RNA and RNP (ribonuclear protein) structure, movement and localization and their associated factors and modifiers; factors derived from microbes (e.g., prokaryotes, eukaryotes and virus) and factors that associate with or modify them can also be used to obtain guide domains.

Guide domains can bind to a target nucleic acid directly, or indirectly such as by binding to a protein that is itself directly or indirectly associated with the target nucleic acid. Antibodies that specifically bind to proteins that can become directly or indirectly associated with a target nucleic acid are one example of a guide domain that indirectly binds to a target nucleic acid.

Common endonuclease domains include the cleavage domain of a restriction endonuclease which has a cleavage domain separate from the recognition domain (HphI, MboII, BbvI, FokI, HgaI, SfaNI, BspMI), activatable endonucleases (Micrococcal endonucleases), and nucleic acids with cleavage activity (ribozymes and the like).

Linker domains are typically polypeptide sequences, such as poly gly sequences of between about 5 and 200 amino acids. In some embodiments, proline residues are incorporated into the linker to prevent the formation of significant secondary structural elements by the linker. Preferred linkers are often flexible amino acid subsequences which are synthesized as part of a recombinant fusion protein. In one embodiment, the flexible linker is an amino acid subsequence comprising a proline such as Gly(x)-Pro-Gly(x) (SEQ ID NO:22) where x is a number between about 3 and about 100. In other embodiments, a chemical linker is used to connect synthetically or recombinantly produced guide and endonuclease subsequences. Such flexible linkers are known to persons of skill in the art. For example, poly (ethelyne glycol) linkers are available from Shearwater Polymers, Inc. Huntsville, Ala. These linkers optionally have amide linkages, sulfhydryl linkages, or heterofunctional linkages.

As described, recombinant guide endonuclease fusion proteins of the invention are preferably made via recombinant ligation of nucleic acids encoding the constituent parts of the fusion protein (e.g., guide, linker and endonuclease) and expression of the resulting construct. Instructions sufficient to direct one of skill through such cloning exercises are found in Sambrook, Berger, Ausubel and Innis, all supra. Generating a guide, linker or endonuclease domain from a known protein, linker amino acid, or endonuclease protein is easily performed by one of skill. Clones for many suitable components are publicly available. Where such clones are not easily obtained from public sources, they are easily made by PCR amplifying the nucleic acid from a biological sample such as a cell, or a genomic or cDNA library, i.e., by designing PCR primers to complement the known nucleic acid sequences (procedures for selecting PCR primers are described supra). Sequences for guide, endonuclease or linker domains, including those exemplified above, are easily found by searching public repositories of nucleic acid sequence. Well-established repositories of sequence information include GenBank™, EMBL, DDBJ and the NCBI, and there are many other databases which are also known. PCR amplified nucleic acids are optionally subcloned to facilitate subsequent processing, or are used as the source for a nucleic acid encoding a guide, endonuclease or linker domain. Once PCR products, or PCR generated subclones, or publicly available clones are obtained, the components are assembled into a contiguous recombinant nucleic acid encoding the chimeric guide endonuclease fusion protein, and the protein made by recombinant expression of the fusion protein.

One of skill will also recognize that a variety of nucleic acid sequences encode any particular polypeptides due to the codon degeneracy present in the genetic code. Each of the nucleic acids which encodes a given polypeptide is described by comparison to the amino acid sequence of the polypeptide and translation via the genetic code to a coding nucleic acid. In preferred embodiments, a nucleic acids which encodes a particular polypeptide is optimized for expression is a particular cell type, such as yeast, humans, etc. by reference to sequence codon bias tables and substitution of a given sequence with a sequence which encodes the same polypeptide using codons preferred for the cell type. This typically increases the level of translation of a given nucleic acid, facilitating expression of the encoded chimeric protein.

Optionally, recombinant components are not synthesized recombinantly, but are instead synthesized chemically, e.g., using a peptide synthesizer, or other solid phase protein synthesis technique. See also, March, supra. Solid phase synthesis of polymers, including biological polymers is known. See, e.g., Merrifield (1963) *J. Am. Chem. Soc.* 85: 2149–2154. Solid-phase synthesis techniques have also been provided for the synthesis of peptide sequences on, for example, a number of "pins." See e.g., Geysen et al. (1987) *J. Immun. Meth*. 102: 259–274. Other solid-phase techniques involve, for example, synthesis of various peptide sequences on cellulose disks supported in a column. See, Frank and Doring (1988) *Tetrahedron* 44: 6031–6040. Still other solid-phase techniques are described in U.S. Pat. No. 4,728,502 and WO 90/00626. Where one or more domain is not a protein, the domain is fused chemically to the other domains, i.e., by standard synthetic chemistry, as described supra.

In one embodiment, the endonuclease is a nucleic acid, which is liked to a guide domain to form the chimeric guide-endonuclease fusion molecule. For example, a variety of ribozymes are well known. A ribozyme is a catalytic RNA molecule that cleaves other RNA molecules having particular nucleic acid sequences. General methods for the construction of ribozymes, including hairpin ribozymes, hammerhead ribozymes, RNAse P ribozymes (i.e., ribozymes derived from the naturally occurring RNAse P ribozyme from prokaryotes or eukaryotes) are known in the art. Castanotto et al (1994) *Advances in Pharmacology* 25: 289–317 provides an overview of ribozymes in general, including group I ribozymes, hammerhead ribozymes, hairpin ribozymes, RNAse P, and axhead ribozymes. In one class of embodiments, the ribozyme RNA recognition domain is deleted, and the cleavage domain is chemically liked (typically via a linker) to the guide domain.

In addition, ribonucleoproteins such as the native RNAse P ribonucleoprotein, can be used as endonuclease domains in the guide endonuclease fusion protein of the invention. These ribonucleoproteins are also typically chemically linked via a linker, to the guide domain.

Similarly, the guide domain is optionally a nucleic acid which hybridizes to the target nucleic acid. In this embodiment, the guide domain is typically chemically linked to the endonuclease domain, using standard synthetic methods. An example of an oligonucleotide being chemically linked to a micrococcal endonuclease protein by chemical coupling is found in Corey et al. (1989) *Biochemistry* 28: 8277–8286.

Where the linker, guide and endonuclease are all nucleic acids (typically RNA), the nucleic acids are typically produced recombinantly, although they are optionally made by synthetic methods, as described, supra, for oligonucleotides using an automated synthesizer.

Pinpoint Detection of In Vivo Protein-DNA Interactions Using a Fok 1 Endonuclease Domain In the process of employing PINPOINT to detect protein-DNA interaction in vivo, a surprising fact was discovered: in vivo, the nuclease domain of Fok 1 predominantly makes single-stranded nicks on the DNA, rather than double strand cuts as expected from the prior art. This critical observation allowed the development of very sensitive techniques to detect in vivo protein-DNA interaction; such a development would not have been possible without this discovery.

In general, these methods utilize ligation or other enzymatic reactions to add an oligonucleotide tag to the site of a Fok 1 nick on the nucleic acid. This tag, in conjunction with subsequent processing steps is used to isolate, detect, and/or purify nucleic acid from the region of the nick.

Pinpoint Detection of In Vivo Protein-DNA Interactions Using A Micrococcal Endonuclease Domain There are drawbacks to the nuclease domain of Fok 1 for in vivo PINPOINT analysis, making chimeric guide-endonuclease fusion proteins with a Fok 1 domain less preferred. First, the nuclease domain at 25 kd is relatively large, potentially causing stearic problems with the guide domain, complicating cloning and the like. Second, the nuclease activity cannot easily be regulated; from the moment a chimeric guide-endonuclease fusion protein comprising a Fok 1 endonuclease is expressed in the cell, it is active. As a result, prolonged expression of the chimeric guide-endonuclease fusion protein (or "pointer") in a cell can be toxic. Lastly, the catalytic rate of Fok 1 nuclease domain is rather low.

For these reasons, we have also developed PINPOINT methods employing micrococcal nuclease chimeric guide-endonuclease fusion proteins in place of Fok 1 fusion proteins. Micrococcal nuclease is smaller in size (16 kd), and therefore causes fewer problems due to interactions with the guide domain. Unlike Fok 1 nuclease, it requires millimolar levels of calcium for maximal activity and therefore it is almost inactive in normal cells, which have nanomolar levels of calcium. Because micrococcal nuclease is inactive, and therefore non- toxic until stimulated with calcium, it is possible to create transgenic cells (both eukaryotic and prokaryotic), plants (yeast, algae, monocotyledons, dicotyledons, etc.) and animals (Drosophilla, mice, rats, livestock, etc.) or stable cell lines expressing a chimeric guide-endonuclease fusion protein having a micrococcal endonuclease domain.

To activate micrococcal nuclease in vivo, the cell membrane is permeabilized with a mild detergent and incubated in a calcium containing buffer for several minutes, resulting in an approximately 10,000 fold increase in activity. Another advantage of micrococcal nuclease is that it leaves unique $_5'$ OH and 3' P ends after cleavage, facilitating purification strategies designed to target these unique cleavage products.

In Vitro Uses for the Chimeric Proteins of the Invention

In one embodiment, the present invention provides specific chimeric guide-endonuclease proteins having an endonuclease domain. These proteins are useful, inter alia, as custom restriction enzymes for the cleavage of nucleic acids. Hybrid affinity cleaving proteins composed of a DNA binding domain of a protein and a Fok1 endonuclease have been used in vitro for cleavage of nucleic acids in a variation of in vitro footprinting methods. See, Chandrasegaran U.S. Pat. Nos. 5,487,994 and 5,436,150; Kim et al. (1996) *Proc. Natl. Acad. Sci. USA* 93:1156–1160 and Kim et al. *Proc. Natl. Acad. Sci. USA* (1994) 91:883–887. One of skill will immediately understand that restriction enzymes having new recognition and/or cleavage sites are very useful tools in techniques relating to cloning and assessing nucleic acids.

The present invention provides a new class of hybrid affinity nucleic acid cleavage proteins having a micrococcal nuclease domain linked via a linker to a guide domain. In addition to the many in vivo uses described herein (see also, commonly assigned U.S. Ser. No. 08/825,664, filed Apr. 3, 1997 and co-filed U.S. Ser. No. 09/054,231, filed Apr. 2, 1998, these chimeric proteins comprising a micrococcal nuclease domain are useful as restriction enzymes in vitro.

As restriction enzymes, these chimeric micrococcal endonuclease fusion proteins have several important advantages over the prior art. First, the micrococcal nuclease domain requires calcium for activation, making it possible to regulate the activity of the protein, in vitro or in vivo. For example, cleavage reactions can be stopped by adding a calcium chelator (e.g., EDTA) to the reaction mixture, or started by adding calcium. One of skill will appreciate that partial digestion of a DNA is sometimes necessary during certain cloning procedures. Second, the position of the cleavage site can be selected relative to the recognition site in the chimeric protein by varying the length of the linker between the micrococcal cleavage domain and the guide domain. Third, micrococcal endonuclease cleaves RNA, giving the chimeric proteins of the invention a unique ability to engineer RNA molecules in cloning procedures. Fourth, under some reaction conditions micrococcal nuclease cleaves only a single strand of a double-stranded nucleic acid, making it possible to selectively cleave, e.g., a single strand on a target DNA, leaving ends which can be modified in subsequent reactions. For example, following kinase or phosphatase treatment, an end left by micrococcal nuclease can be extended using a polymerase, thereby incorporating selected nucleotides into a copy of a target nucleic acid (e.g., radioactive nucleotides used for detecting the copy). Fifth, because the ends made by micrococcal nuclease are unique (leaving a 5' OH and a 3' P) it is possible to use the unique ends as molecular tags for subsequent purification or amplification reactions.

FLASHPOINT Methods

Figure 7:
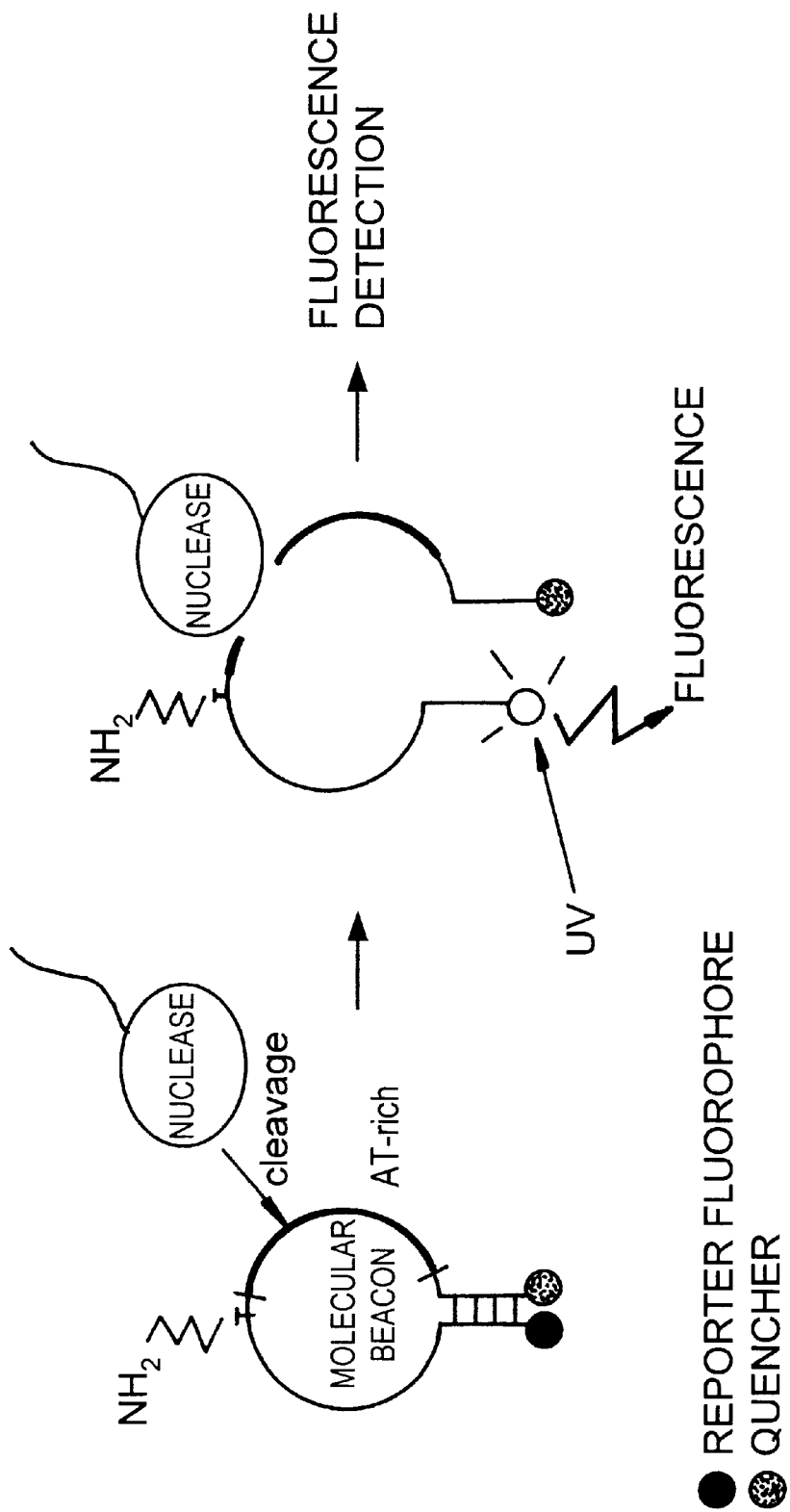
FIG. 7 is a schematic diagram of the FLASHPOINT strategy. The structure of molecular beacon is shown on the left. In the loop portion, the molecular beacon contains an amino-modified ($NH_2$) thymidine (T) and A-T rich nucleotides (thick line). A reporter fluorophore (filled circle) that is excited by UV light and a quencher (gray circle) are present at the 5' and 3' ends of the oligonucleotide, respectively. The nuclease cleaves preferentially in the A-T rich region resulting in the removal of the quencher and emission of fluorescence by the reporter fluorophore.

The invention also provides methods for detecting whether a first molecule is in close proximity to a second molecule. A schematic diagram of the FLASHPOINT methods is shown in FIG. 7. The methods involve attaching a molecular beacon to the first molecule and attaching a chimeric endonuclease to the second molecule. To determine whether the first molecule is in close proximity to the second molecule, one detects whether fluorescence is emitted by a fluorophore present on the molecular beacon. Fluorescence emission is indicative of cleavage of the molecular beacon by the endonuclease moiety, thereby causing separation of the fluorophore and a quencher which is also present on the molecular beacon. Reagents and kits for use in the FLASHPOINT methods are described in more detail in co-filed, commonly assigned U.S. patent application Ser. No. 09/054,231 filed Apr. 2, 1998, which is incorporated herein by reference.

Uses of FLASHPOINT Methods

Figure 8:
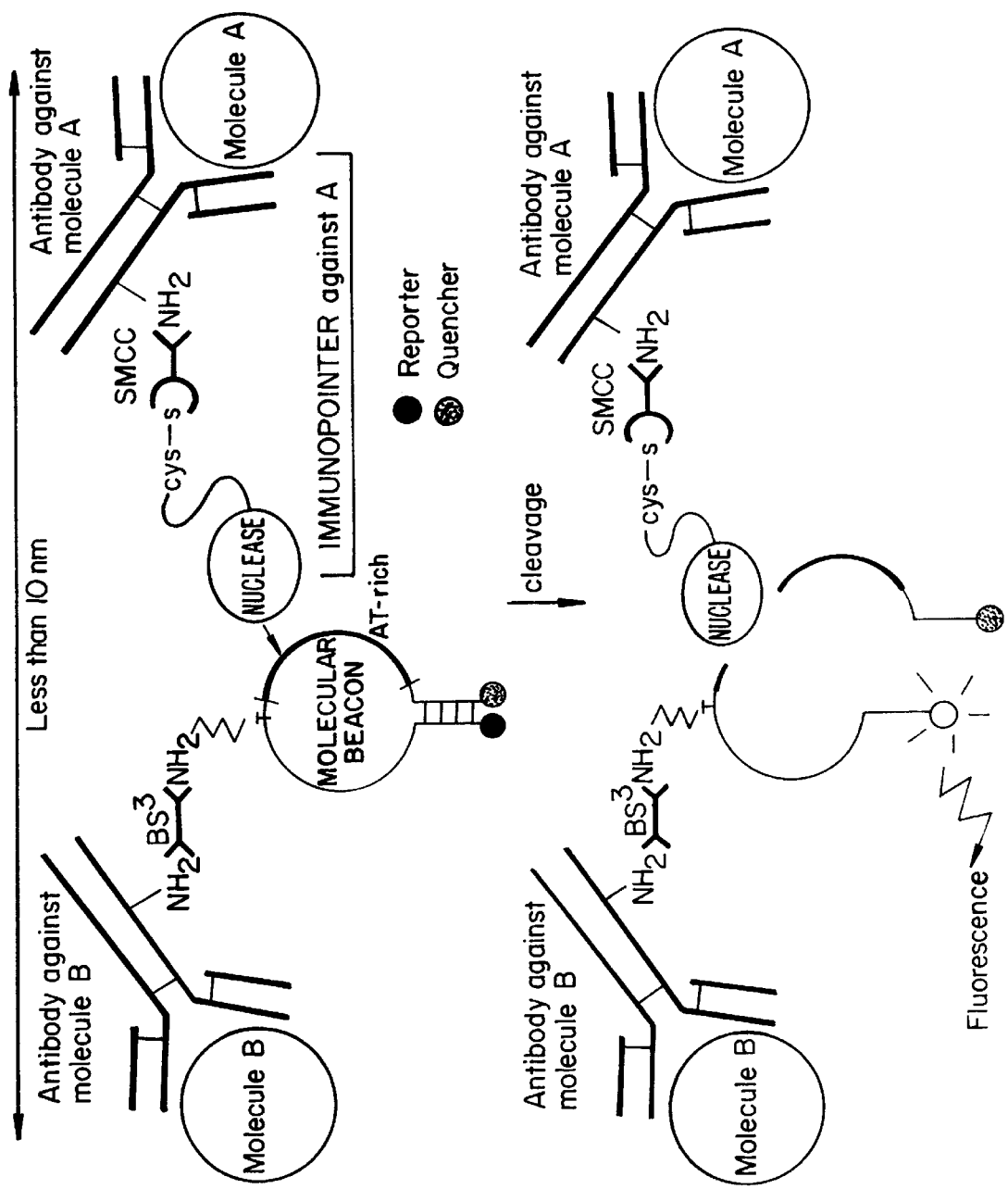
FIG. 8 shows one application of FLASHPOINT to detect proximity of molecules A and B. The position of molecule A is marked by the antibody against molecule A which is crosslinked to the nuclease tail through SMCC (IMMUNOPOINTER), and the position of molecule B is marked by an antibody against molecule B that is crosslinked to the molecular beacon through BS3. If molecules A and B are separated by less than 10 nm, the molecular beacon is cleaved by the nuclease and the reporter fluorophore emits fluorescence (below).

These methods are useful in many types of detection assay which involve detection of intermolecular interactions. Such interactions are involved in many biological and chemical events such as, for example, enzymatic reactions, hormone-ligand interactions, drug or toxin interactions with their receptors, and the like. Moieties from which the first and second molecules can be selected include, but are not limited to, the following binding pairs antigen/antibody, hapten/antibody, hormone/hormone receptor, sugar/lectin, biotin/avidin-(streptavidin), protein A/immunoglobulin, enzyme/enzyme cofactor, enzyme/enzyme inhibitor, enzyme/substrate, protein/modifier, and nucleic acid pairs (DNA-DNA, DNA-RNA or RNA-DNA). One example of the application of FLASHPOINT methods is shown in FIG. 8.

Molecular Beacons

The molecular beacons used in the methods of the invention are typically an oligonucleotide to which is attached a first label and a second label. Most typically, the first and second label interact when in proximity (e.g., due to resonance transfer), and the relative proximity of the first and second labels is determined by measuring a change in the intrinsic fluorescence of the first or second label. Commonly, the emission of the first label is quenched by proximity of the second label. After incubation, the presence or absence of a detectable label emission is detected. The detected emission can be any of: an emission by the first label, an emission by the second label, and an emission resulting from a combination of the first and second label. Typically, a change in the signal due to endonuclease-induced cleavage of the nucleic acid between the labels is detected (e.g., a reduction in quenching which leads to an increase in signal from either or both of the labels, a change in signal color, and the like). For discussion of molecular beacons, see, e.g., Tyagi and Kramer (1996) *Nature Biotechnol.* 14: 303–308.

Many appropriate interactive labels are known. For example, fluorescent labels, dyes, enzymatic labels, and antibody labels are all appropriate. Examples of preferred interactive fluorescent label pairs include terbium chelate and TRITC (tetramethylrhodamine isothiocyanate), europium cryptate and allophycocyanin and many others known to one of skill. Similarly, two colorimetric labels can result in combinations which yield a third color, e.g., a blue emission in proximity to a yellow emission provides an observed green emission. Through use of appropriate fluorophores, molecular beacons can be made in many different colors.

With regard to preferred fluorescent pairs, there are a number of fluorophores which are known to quench one another. Fluorescence quenching is a bimolecular process that reduces the fluorescence quantum yield, typically without changing the fluorescence emission spectrum. Quenching can result from transient excited state interactions, (collisional quenching) or, e.g., from the formation of non-fluorescent ground state species. Self quenching is the quenching of one fluorophore by another; it tends to occur when high concentrations, labeling densities, or proximity of labels occurs. Fluorescent resonance energy transfer (FRET) is a distance dependent excited state interaction in which emission of one fluorophore is coupled to the excitation of another which is in proximity (close enough for an observable change in emissions to occur). Some excited fluorophores interact to form excimers, which are excited state dimers that exhibit altered emission spectra (e.g., phospholipid analogs with pyrene sn-2 acyl chains); see, Haugland (1996) *Handbook of Fluorescent Probes and Research Chemicals*, Published by Molecular Probes, Inc., Eugene, OR., e.g., at chapter 13). DABCYL, a non-fluorescent chromophore, can serve as a universal quencher for many fluorophores used in molecular beacons (Glen Research, Sterling Va.). Methods for attaching DABCYL to oligonucleotides are described in Yoo et al. (1995) *J. Org. Chem.* 60: 3358–3364 and McMinn et al. (1996) *Tetrahedron* 52: 3827–3840; see also, Glen Research 1997 Catalog.

The Forster radius ($R_o$) is the distance between fluorescent pairs at which energy transfer is 50% efficient (i.e., at which 50% of excited donors are deactivated by FRET. The magnitude of $R_o$ is dependent on the spectral properties of donor and acceptor dyes:

$$R_o=[(8.8\times10^{23})(K^2)(n^{-4})(QY_D)(J)(\lambda)]^{1/6}\text{Å}$$

where:
 $K^2$=dipole orientation range factor (range 0 to 4, $K^2=\frac{2}{3}$ for randomly oriented donors and acceptors);
 $QY_D$=fluorescence quantum yield of the donor in the absence of the acceptor;
 n=refractive index; and,
 $J(\lambda)$=spectral overlap integral=$\int \epsilon_A(\lambda)\cdot F_D\lambda\cdot\lambda^4 d\lambda \text{cm}^3\text{M}^{-1}$,
 Where $\epsilon_A$=extinction coefficient of acceptor and $F_D$=Fluorescence emission intensity of donor as a fraction of total integrated intensity.

Some typical $R_o$ are listed for typical donor-acceptor pairs:

| Donor | Acceptor | $R_o$(Å) |
| --- | --- | --- |
| Fluorescein | tetramethylrhodamine | 55 |
| IAEDANS | fluorescein | 46 |
| Fluorescein | Fluorescein | 44 |
| BODIPY | BODIPY | 57 |
| EDANS | DABCYL | 33 |

An extensive compilation of $R_o$ values are found in the literature; see, Haugland (1996) *Handbook of Fluorescent Probes and Research Chemicals* Published by Molecular Probes, Inc., Eugene, OR at page 46 and the references cited therein.

In most uses, the first and second labels are different, in which case FRET can be detected by the appearance of sensitized fluorescence of the acceptor or by quenching of the donor fluorescence. When the first and second labels are the same, FRET is detected by the resulting fluorescence depolarization.

In addition to quenching between fluorophores, individual fluorophores are also quenched by nitroxide-labeled molecules such as fatty acids. Spin labels such as nitroxides are also useful in the liquid phase assays of the invention.

Detection of Intermolecular Interactions

In the methods of the invention, a molecular beacon is attached to a first molecule of the pair of molecules between which an interaction is to be detected. The molecular beacons used in the methods are typically an oligonucleotide to which is attached two labels. As discussed above, the first and second labels on the molecular beacon are spaced such that, upon cleavage between the two labels, the signal resulting from the labels changes (FIG. 7). This can be easily determined empirically for any combination of label pairs, by cleaving the nucleic acids using progressively longer distances between labels (i.e., by increasing the number of nucleotides between the labels), and monitoring the resulting changes in emission properties. As noted above, the literature provides $R_o$ for a large number of label pairs. Typically, the first and second labels will be between about 8 and about 40 nucleotides apart.

The molecular beacon can be attached to a member of the binding pair either directly or indirectly. For example, one can covalently attach the molecular beacon to a molecule of interest. Methods of forming a linkage between an oligonucleotide (such as that which is a component of the molecular beacon) and other types of molecule are known to those of skill in the art. One suitable method involves incorporating into the molecular beacon (preferably in the loop portion) an amino-dT residue. This is then conjugated using a chemical linker to a functional group (e.g., an amine group) on the molecule of interest (see, e.g., Partis et al. (1983) *J. Prot. Chem.* 2: 263–277). Alternatively, the molecular beacon can be attached to the molecule of interest indirectly by noncovalent means. For example, the molecular beacon can be attached to a binding moiety (e.g., an antibody) that binds to the binding pair member of interest.

According to the methods of the invention, proximity between a first molecule and a second molecule is detected by cleavage of the molecular beacon attached to the first molecule by an endonuclease moiety attached to the second molecule. Suitable endonuclease moieties, including those in which endonuclease activity is inducible (e.g. by calcium) are discussed in detail above. The attachment of the endonuclease moiety to the second molecule or to the binding moiety can be either direct (e.g., covalent) or indirect. Methods for direct chemical conjugation are known to those of skill in the art and include, for example, use of a heterobifunctional linker. Suitable linkers are known to those of skill in the art. One example of a suitable linker is the heterobifunctional linker SMCC (succinimidyl 4-[N-maleimidomethyl]cyclohexane-1-carboxylate; Sigma Chemical Co., St. Louis, Mo.), which can form a link between an amino residue (for example, lysine) and a thiol (such as that provided by cysteine). Other cross-linkers include, for example, m-maleimidobenzyl-N-hydroxysuccinimide ester (MBS) (Liu et al. (1979) *Biochemistry* 18: 690; Green et al. (1982) *Cell* 28: 477), glutaraldehyde, a carbodiimide succinyl anhydride, N-succinimidyl-3-[2-pyridyldithio]-propionate, and the like.

The endonuclease moiety also can be attached to the second molecule indirectly, e.g., by attachment to a binding moiety that can bind to the second molecule. For example, one can attach the endonuclease moiety to an antibody that binds to the molecule of interest. Attachment of the endonuclease moiety to either the second molecule of the binding pair, or to a binding moiety, should not interfere with the enzymatic activity of the endonuclease and should provide rotational freedom for the endonuclease domain. Thus, in a preferred embodiment, the endonuclease moiety is attached by way of a flexible tail such as, for example, a flexible linker. Linkers can be, for example, flexible amino acid chains that are attached to the endonuclease domain, and/or chemical linkers of suitable length. The linker can be of any desired length, with a shorter length resulting in higher resolution due to the requirement for closer proximity of the molecular beacon associated with the first molecule and the endonuclease associated with the second molecule. In preferred embodiments, the methods can detect two molecules that are separated by approximately 50 nm or less, more preferably about 10 nm or less, and most preferably about 1 nm or less.

Where the endonuclease moiety is to be attached to a polypeptide, a preferred method of attachment is to construct a gene that encodes a fusion protein which includes both the endonuclease moiety and the binding moiety or the molecule of interest. Methods of constructing and expressing genes encoding fusion proteins are known to those of skill in the art. In a preferred embodiment, the chimeric gene also encodes a flexible polypeptide linker between the endonuclease moiety and the binding moiety.

The FLASHPOINT methods of the invention are useful for detecting intermolecular interactions in vitro, in situ, and in vivo. For example, one can use the methods to detect intermolecular interactions that occur within a cell, tissue, or organism. In some embodiments, the cells or tissues can be fixed, embedded, and/or sectioned by methods known to those of skill in the art (see, e.g., Ausubel et al., supra.). The molecular beacon and the endonuclease domain are added to the sample and allowed to bind to their respective target molecules. In preferred embodiments in which an inducible endonuclease moiety is used, endonuclease activity is induced after binding has occurred. If the target molecules are in close proximity, the endonuclease cleaves the molecular beacon, thus resulting in emission of a signal. The signal can be localized using, for example, fluorescence microscopy.

Figure 9:
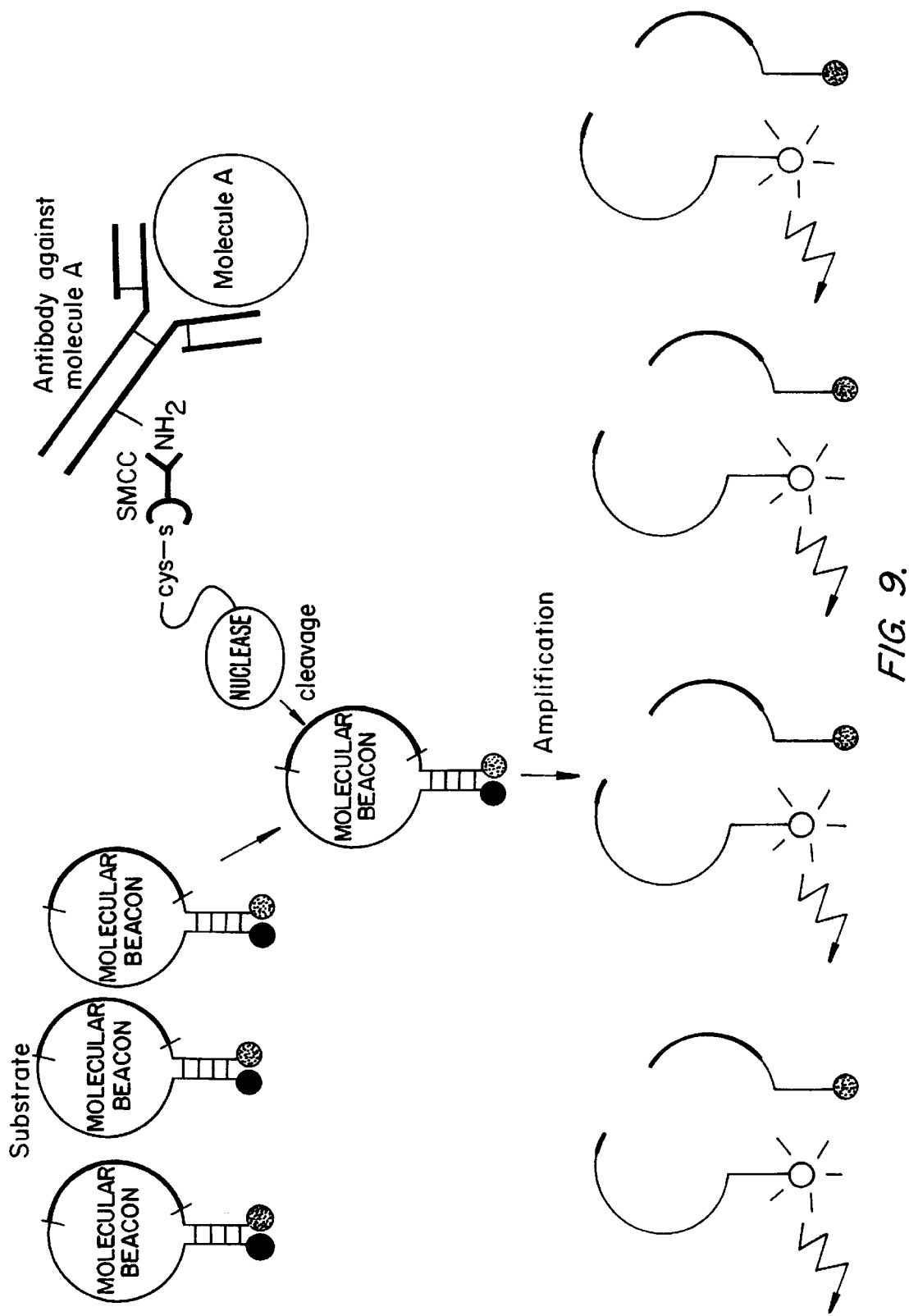
FIG. 9 shows the fluorescence amplification method provided by the invention. The IMMUNOPOINTER against molecule A cleaves free molecular beacon (substrate) resulting in the accumulation of fluorescence emitting reporter.

The invention also provides methods by which one can determine whether the absence of a signal is due to poor binding of the chimeric endonuclease and/or the molecular beacon to their respective target molecules, rather than being due to the target molecules not being in close proximity. In these embodiments, either or both of the chimeric endonuclease and the molecular beacon-containing moiety are labeled with a fluorophore of different excitation and emission wavelengths than the beacon. These labels are then visualized, e.g., with a fluorescence microscope. The presence of a signal from the fluorescent labels attached to the chimeric endonuclease and the molecular beacon-containing moiety, but not a signal from the molecular beacon itself, indicates that the target molecules are not in close proximity. Amplification of Signals from Immunohistological Methods Also provided by the invention are methods of obtaining greater sensitivity in immunohistological techniques. A schematic diagram of these methods is shown in FIG. 9. The methods offer significant advantages over previously known methods for detecting target molecules, particularly where localization of target molecules is desired. High resolution localization of a molecule by microscopy, for example, is typically performed using confocal laser microscopy. This requires the use of fluorophore-tagged antibodies; because the fluorophores are directly conjugated to the antibodies, the emitted fluorescence cannot be amplified, thus resulting in a relatively weak signal in many cases. The methods of the invention overcome this drawback by providing a means by which a fluorescent signal can be amplified, thus increasing sensitivity.

In the methods of the invention, a target molecule is contacted with a chimeric endonuclease which binds to the target molecule. The chimeric endonuclease is then contacted with a molecular beacon. The endonuclease can cleave multiple molecular beacons that come into contact with the endonuclease moiety, thus resulting in amplification of the fluorescence signal. To maximize the signal, fluorescence is integrated over time.

In a typical embodiment, the methods involve preparation of a slide of tissue or cells and treating the slide with a primary antibody, as is done in conventional immunofluorescence assays. Instead of detecting the primary antibody by use of a fluorophore-tagged antibody, for example, the primary antibody is contacted with a detection moiety, termed an "immunopointer," that binds to the primary antibody and includes an endonuclease domain, preferably one that is inducible. Upon binding of the immunopointer to the primary antibody, a molecular beacon is added and endonuclease activity is induced.

EXAMPLES

The following examples are provided by way of illustration only and not by way of limitation. Those of skill will readily recognize a variety of noncritical parameters which could be changed or modified to yield essentially similar results.

Example 1

Identification of Protein Position on Target Plasmid DNA (FIG. 1) Using a Chimera Comprising a Micrococcal Endonuclease Domain (Pinpoint-MNase)

In one embodiment, the invention provides methods of cleaving and detecting a target plasmid nucleic acid in vivo. This is useful, inter alia, for monitoring the interaction between a chimeric guide protein and a selected target nucleic acid. For example, the interaction between a transcription factor guide domain and a promoter target nucleic acid can be monitored. This facilitates the study of gene expression, and provides a basis for screening for the effect of potential therapeutic agents on transcription factor activity. For example, using a p53-endonuclease chimera, it is possible to screen for agents which modulate p53 activity.

An expression vector encoding a chimeric guide-micrococcal endonuclease fusion protein is transduced or injected into cells. The chimeric fusion protein optionally comprises a oligonucleotide region between the guide and micrococcal domains, such as a polyglycine sequence.

Approximately 16–48 hours after transduction, the cells are isolated and transduced for a second time with the target plasmid DNA containing a potential target site recognized by the chimeric guide-micrococcal endonuclease fusion protein. Approximately 2 to 48 hours after the second transduction the cells are permeabilized with a mild detergent such as lysolecithin or NP-40 in the presence of 2 mM exogenous calcium for 1–10 minutes to activate the MNase domain on the expressed chimeric protein. The target DNA (along with other low molecular weight DNA) is recovered using a standard Hirt preparation protocol. See, e.g., Anant and Subramanian (1992) *Methods in Enzymology* 216, 20–29.

The nick created by the chimeric protein (called the "target cleavage site" or "point") in the target nucleic acid is converted to a double stranded blunt end by primer extending with an oligonucleotide primer (see, FIG. 1). The blunt end is marked by ligating a trapping oligonucleotide after phosphorylating the 5' OH end created by the MNase domain of the chimeric protein. A fragment marked by ligation of the trapping oligonucleotide is amplified with PCR using an internal primer and a second primer which is derived from a sequence in the trapping oligonucleotide. The amplified fragment is then detected with one of a number of different strategies, such as primer extension with a labelling primer (e.g., radioactively or fluorescently labelled), Southern blot analysis, or nested PCR. In many cases, primer extension with the labelled oligonucleotide primer is sufficient to detect the point.

One way of marking the 3' end of a point is to extend it with terminal transferase after dephosphorylating it. A dephosphorylation step is used because MNase leaves a 3' phosphate end, which cannot be extended by terminal transferase or by ligation. The 3' end can also be marked by ligating a single stranded oligonucleotide. Fragments thus marked are PCR amplified with a primer made complementary to the sequence added on the 3' end, and a primer from a known internal site.

Example 2

Identification of a Position on a Known Genomic Region Using a Chimera Comprising A Micrococcal Endonuclease Domain In one embodiment, the invention provides methods of cleaving and detecting a target nucleic acid from a known genomic sequence in vivo. This is useful inter alia, for determining whether a selected genomic nucleic acid is bound by a particular chimeric guide protein. For example, the interaction between a transcription factor guide domain and a promoter target nucleic acid can be monitored. This facilitates the study of gene expression, and provides a basis for screening for the effect of potential therapeutic agents on transcription factor activity. For example, using an Sp1-endonuclease chimera, it is possible to screen for agents which modulate Sp1 activity. Similarly, the effects of any potential modulator of a transcription factor oncogene such as c-myc can be assessed.

Figure 2:
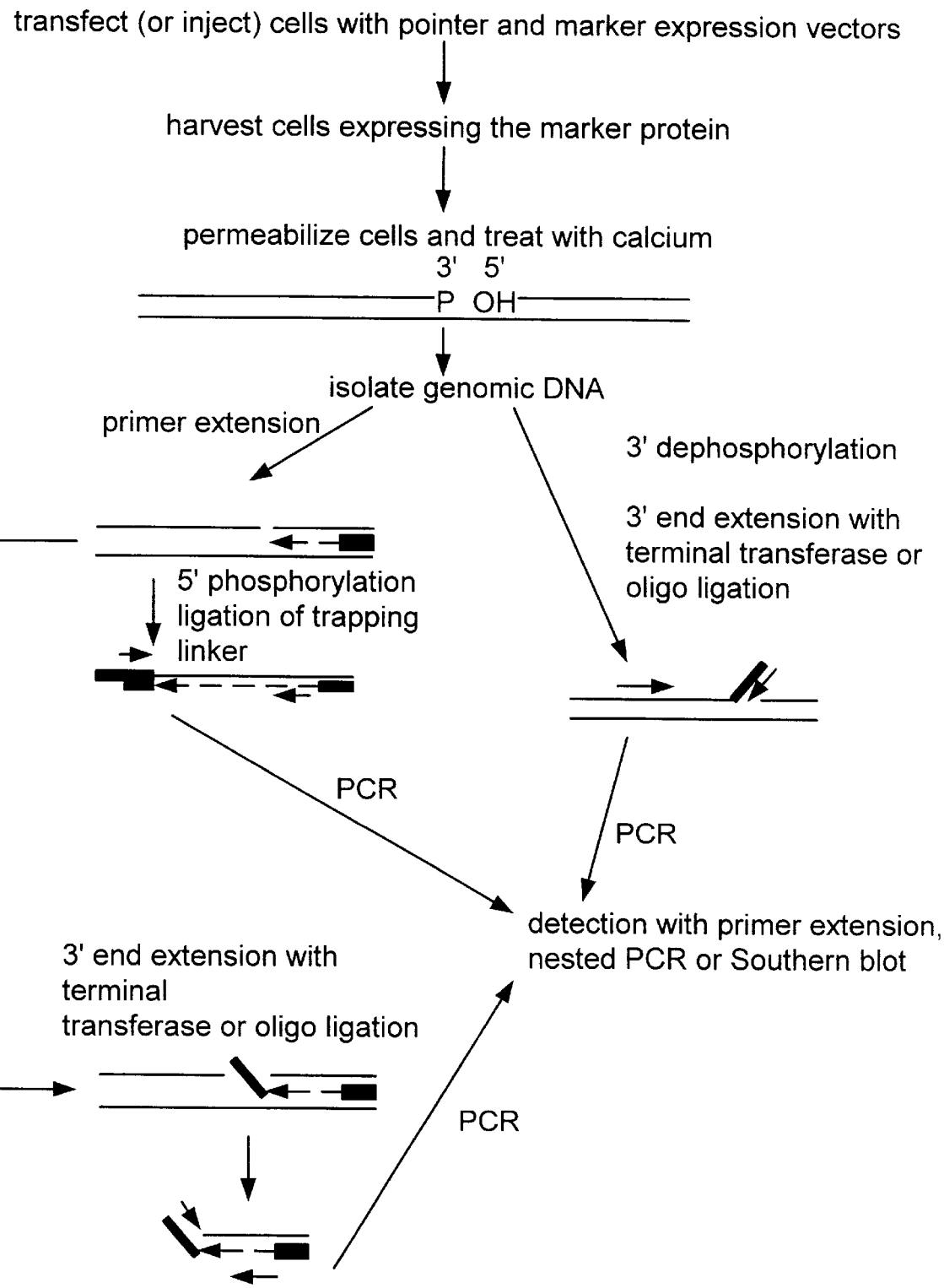
FIG. 2 is a schematic drawing of a method of detecting a genomic target nucleic acid in vivo.

The expression vector for the chimeric guide endonuclease fusion protein is either transiently or stably transduced into cells (see, FIG. 2). If cells are transiently transduced, the chimeric guide endonuclease fusion protein expression vector is cotransduced with an expression vector for a marker gene such as GFP (green fluorescent protein). Cells that express GFP, and therefore most likely express the chimeric guide endonuclease fusion protein, are isolated by FACS (fluorescence activated cell sorting) or HOOK.

This step facilitates selection of transiently transduced cells. Transduction efficiency for most cells, and most transduction procedures is approximately 10% and, therefore, a selection step as described is used to ensure that a higher percentage of cells under analysis include the chimeric guide endonuclease fusion protein. Alternatively, a selection step is not required for stable cell lines since every cell expresses the chimeric guide endonuclease fusion protein.

After chimeric guide endonuclease fusion protein expressing cells are isolated, they are permeabilized with a mild detergent such as lysolecithin or NP-40 and incubated for 2 to 5 minutes in calcium activation buffer to activate the MNase before adding a stop buffer (containing EDTA or Zinc). Subsequent steps starting with primer extension are similar to Example 1, with the additional step of physical isolation of DNA fragments prior to PCR. Although different strategies are possible, labelling the trapping oligonucleotide with biotin and isolating trapped DNA fragments with streptavidin magnetic beads is a favored way of isolating DNA fragments. This isolation step decreases the background signal from PCR amplification of unmarked DNA.

Example 3

Identification of Chimeric Guide Endonuclease Fusion Protein Binding to an Unknown Genomic Target (Differential PINPRINT)

PINPOINT-MNase can be used to scan all genomic positions of a chimeric guide endonuclease fusion protein simultaneously. The chimeric guide endonuclease fusion protein is expressed and expressing cells isolated as described in Example 2. In order to minimize shearing which can produce unwanted background of cleaved sites, the genomic DNA is isolated while the cells are embedded in an agarose plug. After purification, agarose-embedded genomic DNA is digested with a restriction enzyme such as Nco 1 to minimize shearing in subsequent steps. Since MNase created cleavage sites are distinguished from endogenous nuclease induced cleavage sites by the 3' P and 5' OH ends that MNase generates, it is important to reduce shearing as much as possible, because shearing of the DNA can also create 3' P and 5' OH termini.

Although the digestion with Nco1 creates cleaved ends, these are eliminated later based on the Nco 1 recognition sequence, and, therefore, are not problematic. Since the nicks created by MNase cannot be ligated using a standard ligase, a ligase is added to seal nicks that have 5' P and 3' OH ends to reduce background in subsequent amplification reactions.

Figure 3:
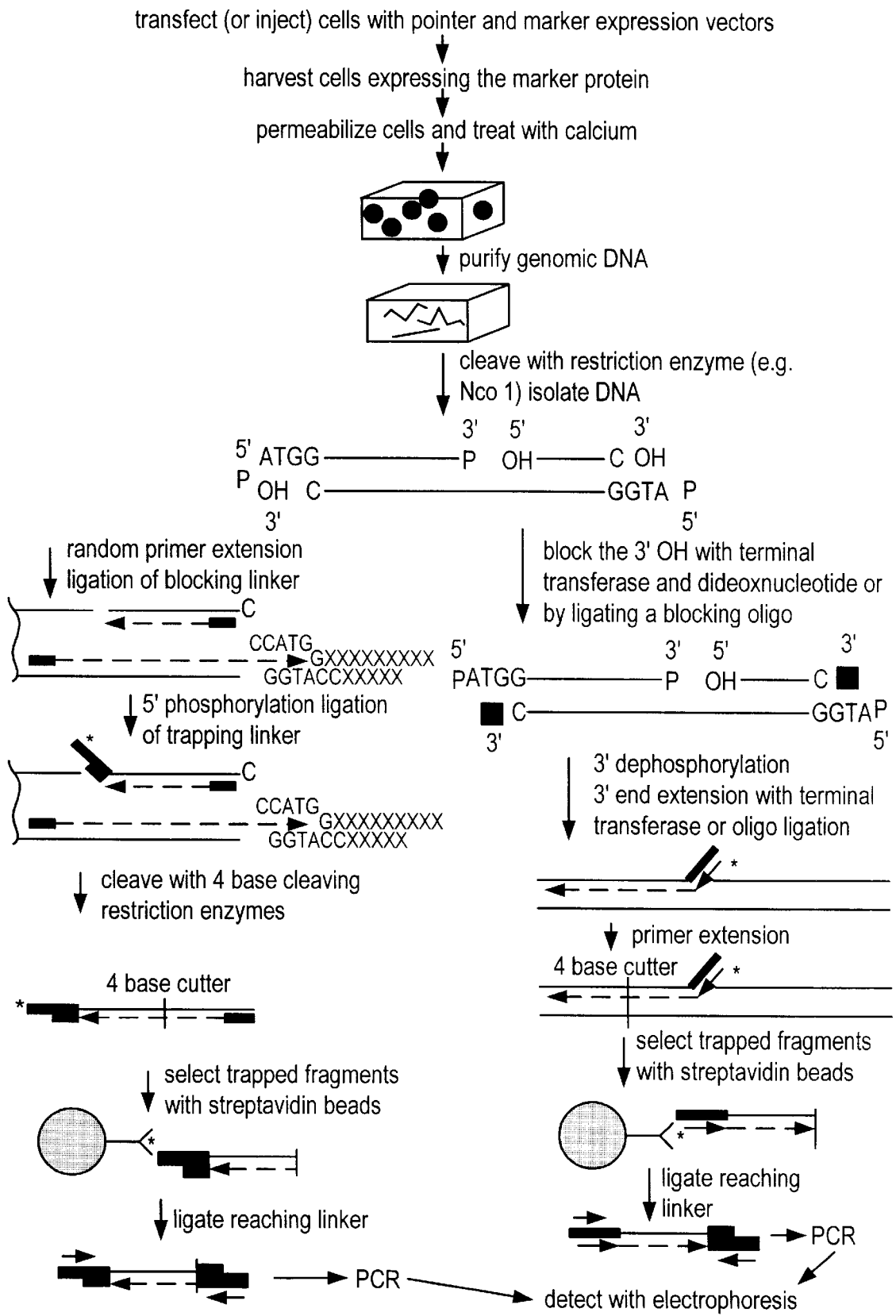
FIG. 3 is a schematic drawing of a method of detecting an unknown genomic target nucleic acid in vivo (SEQ ID Nos:20 and 21).

Any nicks in the genomic DNA created by the chimeric guide protein are onverted to double stranded blunt ends with primer extension using random primers (see, FIG. 3). The blunt ends having 5' P and 3' OH ends are blocked by ligating blocking linker oligonucleotides, which only ligate to ends with a 5' P, leaving MNase specific nicks intact. At this point, only the ends with the 5' OH are available for ligation. After phosphorylation of the 5' OH end, a biotinylated trapping linker oligonucleotide is ligated to the resulting 5' P. Unligated trapping oligonucleotide is discarded. After the trapped fragments are isolated as above (see, Example 2) using streptavidin beads, they are cleaved with a pair of 4 base cutting restriction enzymes (such as Alu1 and Rsa1) that leave blunt ends. A reaching linker oligonucleotide is then ligated to the blunt ends. The fragments that are bracketed with a trapping oligonucleotide and a reaching oligonucleotide are amplified by PCR using a primer that is complementary to the trapping linker oligonucleotide and a primer that is complementary to the reaching linker oligonucleotide.

Since the positions of the 4 base cutting restriction enzymes are different relative to each nick created by the chimeric guide-endonuclease fusion protein, electrophoresis of the amplified fragments results in a ladder pattern on the electrophoretic gel. By comparing ladders for different chimeric guide-endonuclease fusion proteins side by side, one can distinguish chimeric guide-endonuclease fusion proteins specific bands from non-specific bands. The specific bands are cut out of the gel, reamplified with PCR and cloned.

A similar strategy for identifying the 3' side of a target cleavage site using either terminal transferase extension or oligo ligation is shown on the right side of FIG. 3. In this protocol, the 3' OH generated by the restriction enzyme (e.g., Nco 1) is extended using either a terminal transferase, or a blocking oligonucleotide. After 3' dephosphorylation of the 3' phosphate at the target cleavage site made by the chimeric guide-endonuclease fusion protein, the 3' end is extended with a terminal transferase, or by ligating an extension oligonucleotide to the end. Double-stranded DNA is made by primer extension using a biotynylated oligonucleotide complementary to the blocking oligonucleotide, or complementary to the end made using terminal transferase. A restriction enzyme with a four base recognition site is used to cleave the double-stranded DNA. The resulting cleaved DNA is isolated on streptavidin beads. A reaching oligonucleotide linker is ligated to the isolated DNA, and the isolated DNA is amplified using primers complementary to the reaching linker and complementary to the biotinylated ligonucleotide. This amplified DNA is detected and/or cloned for subsequent analysis.

Example 4

Identification of Protein Position on Unknown Genomic Target (Point Directory)

Figure 4:
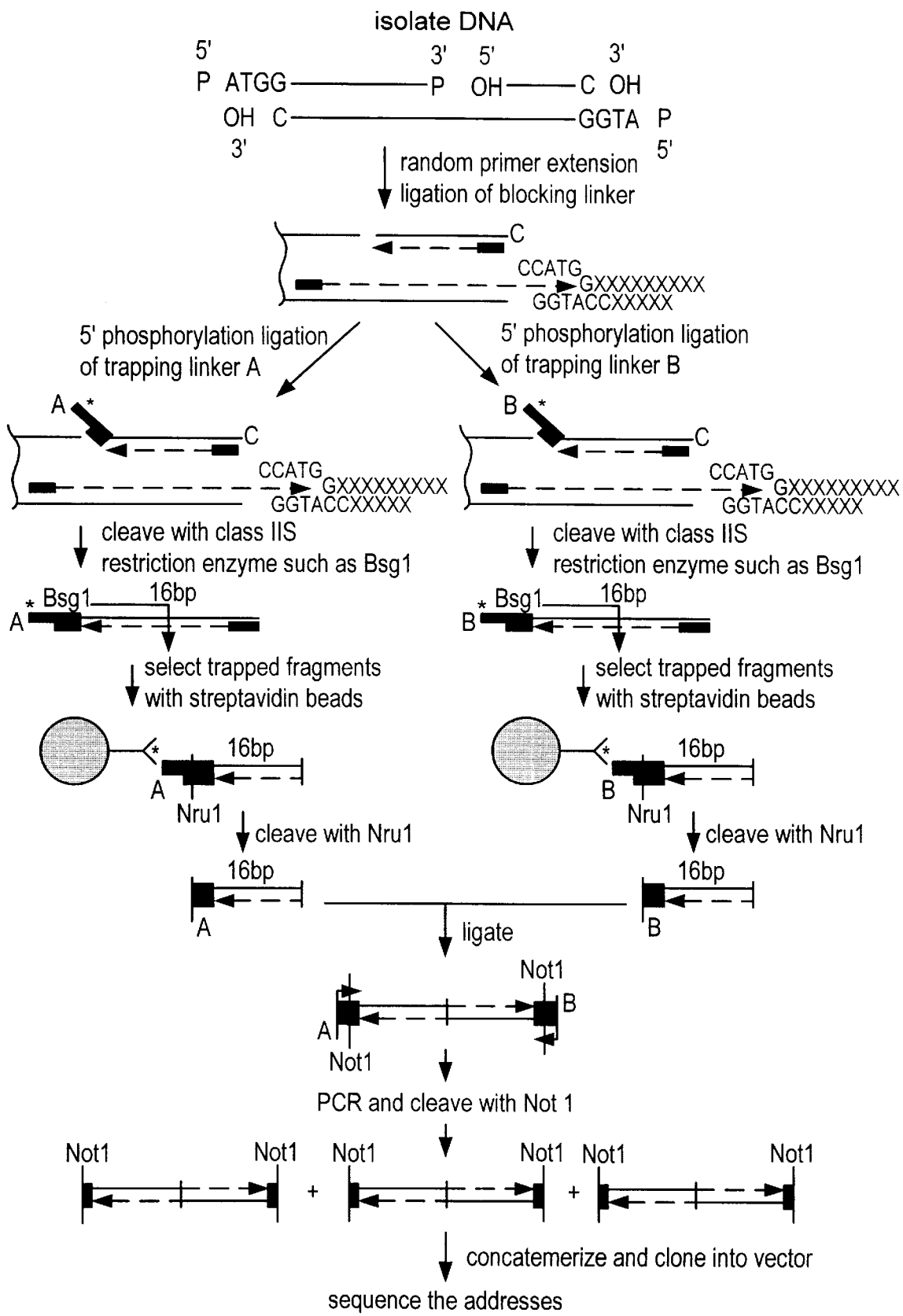
FIG. 4 is a schematic drawing of a method of making a directory of addresses of unknown genomic target nucleic acids in vivo (SEQ ID Nos:20 and 21).

A more comprehensive way to determine the genome-wide positions which are cleaved by a chimeric guide-endonuclease fusion protein is to create a "point directory," i.e., a library of nucleic acids corresponding to many of the target cleavage sites (points). The steps for this technique is same as that of Example 3 until ligation of the trapping linker oligonucleotide (see, FIG. 4). After phosphorylation of primer extended DNA, a blocking linker oligonucleotide is ligated to block all ends having a 5' P. Half of the sample is ligated to trapping linker oligonucleotide A and the other half is ligated to trapping linker oligonucleotide B. These two trapping oligonucleotides contain the recognition sequence for a class IIS restriction enzyme, such as Bsg1, which cleaves 16 bp 3' to the enzyme's recognition sequence. Thus, cleaving the trapped DNA with Bsg1 leaves a 16 bp subsequence (termed an "address") of the target cleavage site attached to the respective trapping linker. Fragments cleaved by the class IIS restriction enzyme are physically isolated, e.g., with magnetic streptavidin beads. Isolated DNA fragments are then separated from the magnetic beads by cleaving within the trapping linker with a restriction enzyme whose cleaves site is found within the linker (e.g., Nru1). The liberated DNA fragments attached to the two trapping linkers are then ligated together. The ligated fragments are amplified with PCR using primers A and B. The amplified fragments are cleaved with a second restriction site found within the cleaved linker (e.g., Not 1) and ligated into a concatemer and cloned into a plasmid vector such as the universally available pBluescript II. Plasmid DNA containing the concatemers is isolated and sequenced from the opposite ends of the concatemer. The concatemers will contain two point-addresses separated by a restriction site (e.g., a Not 1 site).

The addresses are compiled and the location identified by searching the genomic sequence databases, or by using the addresses to make probes to screen genomic libraries.

PINPOINT is useful not only for identifying positions of static proteins bound to DNA or near DNA (i.e. tethered by protein-protein interaction), but those with processivity as well. Because the position of a processive RNA polymerase is reflective of the transcriptional status of that gene, one can compile the point-addresses of RNA polymerase, and therefore its transcriptional status, using the techniques above. The conventional analysis of the steady state cytoplasmic RNA levels, e.g., by northern analysis, reflects not only transcription but posttranscriptional modification (such as splicing), RNA transport and stability, and does not reliably reflect the transcriptional status of a promoter at any given time. In order to understand gene expression, it is useful to have the capability to monitor all variables at play at any given moment during gene expression, starting from the recruitment of transcription factors. This ability is provided by the above techniques.

MNase also cleaves RNA in the presence of calcium, leaving a 5' OH and 3' P ends. After reverse transcription, strategies similar to those described for DNA are applied to detecting the positions of RNA binding proteins such as one of EIF-4 proteins which are important for translation of mRNA. By compiling a directory of the EIF-4 addresses, one can determine the translational status of all the mRNA in a cell at any given moment.

Example 5

PINPOINT-Fok

Like MNase, the nuclease domain of Fok1 creates single stranded nicks on DNA in vivo; unlike MNase, however, it leaves a 5' P and 3' OH at the cleavage site. These ends are extended with terminal transferase without dephosphorylation of the 3' end, or ligated directly to a trapping linker oligonucleotide without phosphorylation of the 5' end, after primer extension and Klenow treatment, or Klenow treatment alone. Identification of the points created by the nuclease domain of Fok 1 can be done as described for MNase above.

Example 6

Figure 5:
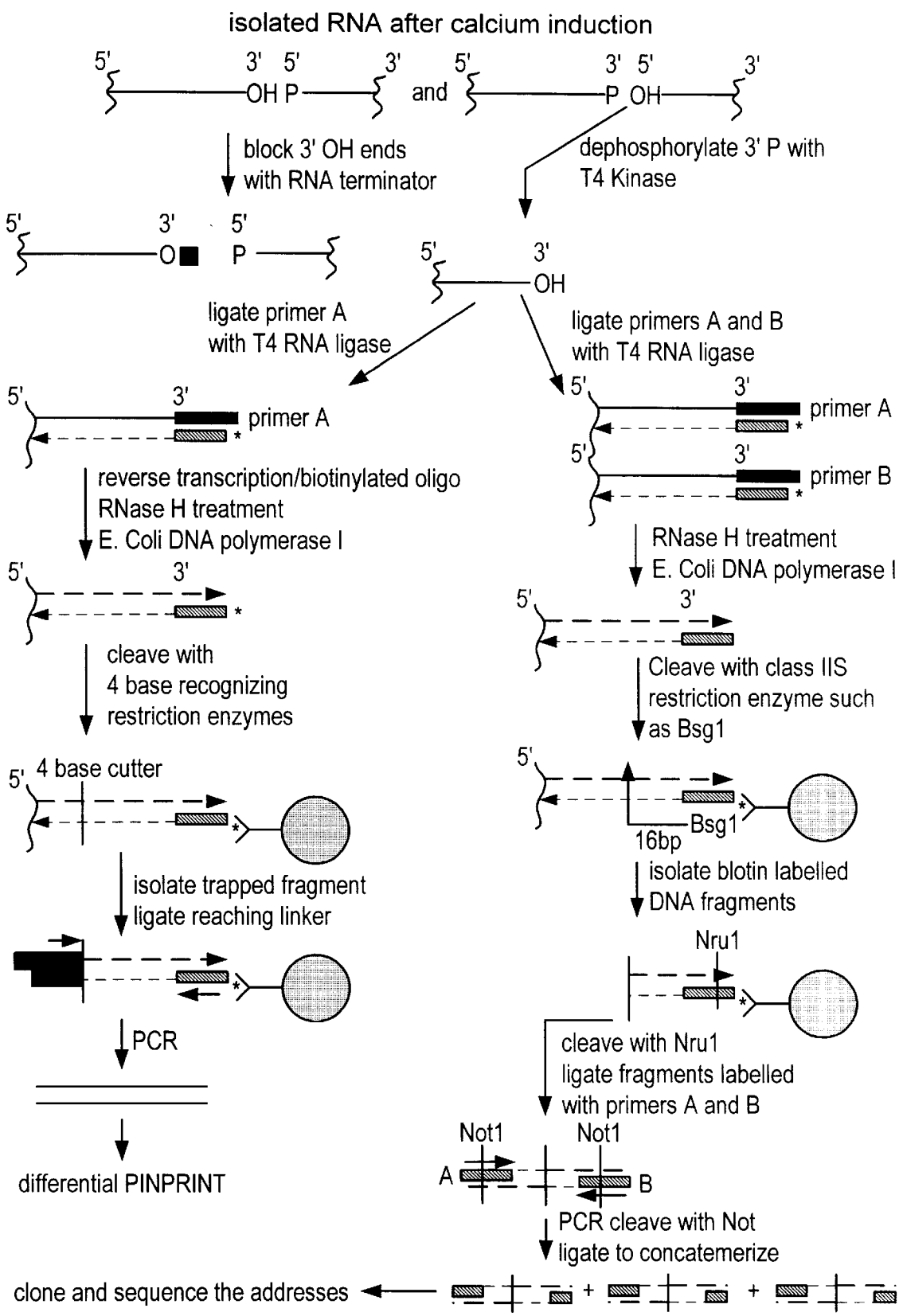
FIG. 5 is a schematic drawing of a method of detecting an RNA target nucleic acid in vivo.

PINPOINT for RNA Point Detection (FIG. 5)

Since MNase also cleaves RNA in the presence of calcium, leaving a 5' OH and a 3' P end, PINPOINT strategies are also used to identify RNA binding sites for both known and unknown RNA binding proteins. The strategies are similar to those described for DNA binding proteins in FIGS. 1 through 4 and examples 1–5, with a few modifications. The strategies that correspond to the DNA strategies in FIGS. 1 and 2 are different primarily in that they use a primer of known sequence for reverse transcription.

After RNA cleavage by a chimeric protein comprising an MNase cleavage domain which cleaves RNA is induced with calcium, RNA is isolated and all the 3' OH ends are first blocked with T4 RNA ligase and terminating ribose nucleotides such as 3'-O-Methylguanosine 5' Triphosphate. Once the terminating nucleotide is added to the 3' end, it is no longer available for further ligation or extension. The remaining 3' P ends, created by MNase, are dephosphorylated with T4 polynucleotide kinase or a phosphatase enzyme. The 3' OH ends are marked by ligating primer A with RNA ligase or half of the sample with primer A and half with primer B for differential PINPRINT or point directory strategies outlined in the examples above, respectively. Using a biotinylated primer complementary to the ligated primer, double stranded cDNA is made. The biotinylated DNA fragments are isolated with streptavidin beads as described earlier. The remaining steps for both differential PINPRINT and point directory are identical as for identifying points on DNA.

Example 7

ImmunoPINPOINT

In one aspect, the present invention provides chimeric protein comprising an antibody, or a recognition domain derived from an antibody, attached via a linker domain to a micrococcal endonuclease domain. The antibody recognizes either a protein which binds, directly or indirectly, to a nucleic acid, or a primary antibody which binds, directly or indirectly, to the nucleic acid.

Figure 6:
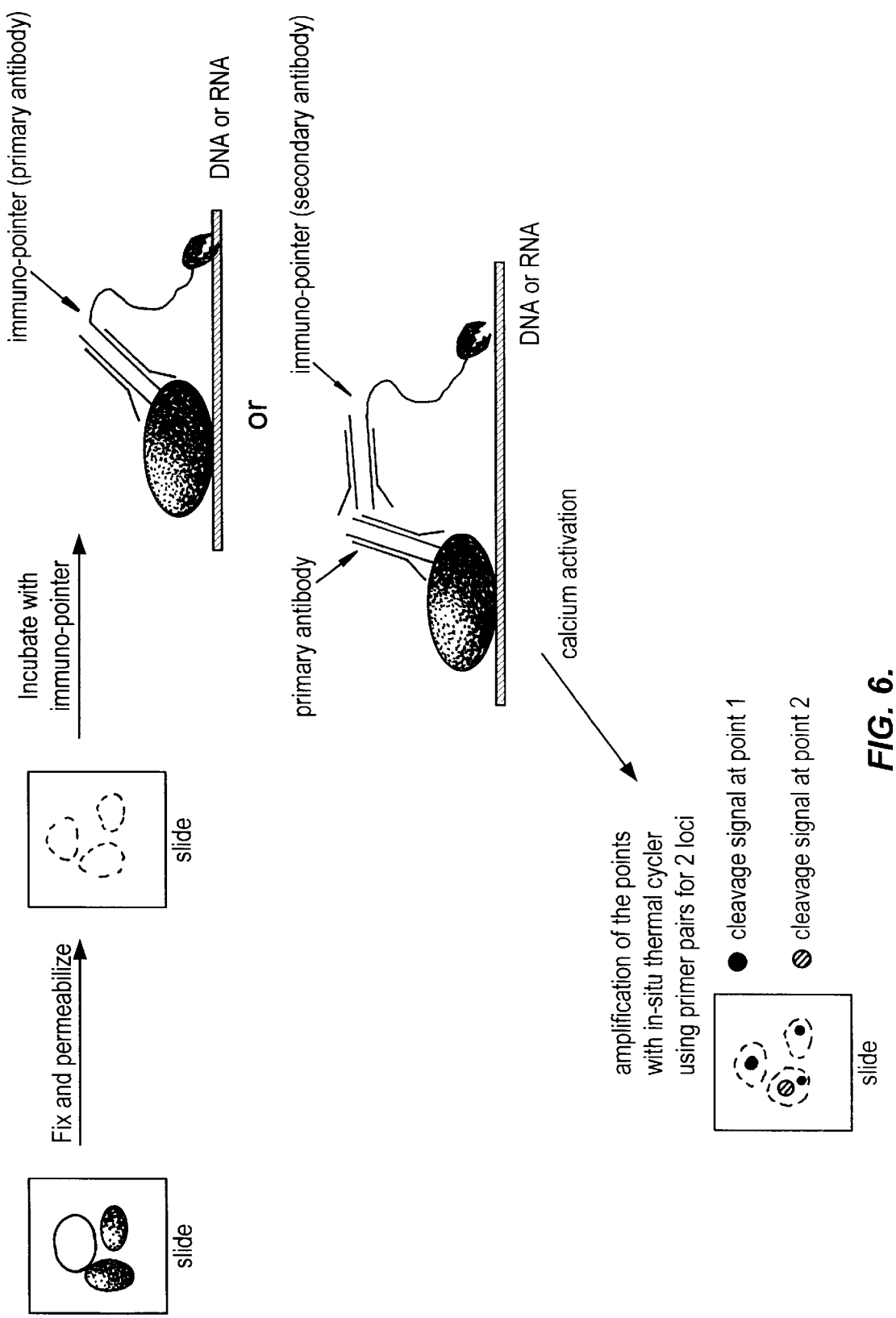
FIG. 6 is a schematic drawing of a method for detecting target nucleic acids using a chimeric protein comprising an immunoglobulin.

Cells comprising a target nucleic acid are fixed and permeabilized. The fixed, permeabilized cells are then incubated with a chimeric guide endonuclease protein, where the guide domain is derived from an immunoglobulin. In embodiments where the immunoglobulin recognizes a protein bound to a nucleic acid, the immunoglobulin guide domain binds to the protein bound to the nucleic acid, and positions the chimeric protein near the binding site. After calcium activation, the cleavage domain cleaves the nucleic acid, which is then amplified or detected in the same manner as described supra. See also, FIG. 6.

In embodiments where the immunoglobulin guide domain recognizes a primary antibody, the cells are incubated with both the chimeric protein and the primary antibody. The primary antibody binds to a protein bound to the nucleic acid and the immunoglobulin guide domain positions the chimeric protein near the binding site by binding to the primary antibody. After calcium activation, the cleavage domain cleaves the nucleic acid, which is then amplified or detected in the same manner as described supra. See also, FIG. 6.

Although this example is described for an application using an immunoglobulin guide domain, it will be appreciated that similar in situ methods are also provided for guide domains other than antibodies by substitution of alternate guide domains in the method.

Example 8

PINPOINT Analysis of the Globin LCR

A locus control region (LCR) confers high level, position-independent expression of a linked gene (see, Orkin (1995) *Eur J Biochem* 231:271–81). The best characterized among these is the β-globin LCR which serves as the master regulatory element for the expression of the globin family of genes in a locus that spans almost 100 kb (Orkin, id.). The expression of the globin family of genes in erythroid cells are developmentally regulated. In human, the ε-globin gene is expressed first in the embryo, followed by the gamma globin genes in the fetus, and the β-globin gene at birth and throughout life. Proper expression of all these genes is dependent on the LCR, which resides in four DNase 1 hypersensitive sites (5'HS1–5) located upstream of the ε-globin gene. The complete set of these hypersensitive sites is required for full position-independent expression suggesting that they act synergistically. These DNaseI hypersensitive sites contain a number of binding sites for CACCC and E box binding factors, GATA-1 and NFE-2 as well as yet uncharacterized factors (Talbot and Grosveld (1991) *EMBO J.* 10:1391–8).

The LCR-globin promoter interaction, presumably mediated by these factors for which binding sites are present in the LCR, appears to be dynamic during development. For example, LCR-mediated expression shifts back and forth between two genes (e.g., gamma- and β-globin) during the switch from gamma-globin to β-globin gene expression before settling on stable β-globin expression. The LCR-linked β-globin gene is expressed even when it is embedded in heterochromatin, suggesting that the LCR also opens the chromatin, perhaps by recruiting chromatin modifying complexes such as NURF or BRG1. Indeed, in Hispanic thalassemia where the LCR is deleted, the chromatin of the whole β-globin domain is condensed. As a result, the promoter regions, which are nucleosome free in the presence of the LCR, are occupied by nucleosomes. Perhaps as a related phenomenon, the β-globin domain no longer replicates early in S phase but late.

The molecular mechanism by which the β-globin LCR activates transcription is not known, but a number of studies have shown that minimal promoter elements play an important role (Antoniou and Grosveld (1990). *Genes Dev* 4:1007–13). The β-globin promoter region can be divided into two regions, upstream (−110 to −815) and minimal (1 to −110). The upstream region contains, among others, GATA-1 and NF 1 binding sites and a CAAT box. The minimal promoter region contains two CACCC (distal and proximal), one CAAT and one TATA boxes. In the presence of the LCR, the minimal promoter is sufficient for maximal expression. Mutation of the proximal CACCC box and or CAAT box severely weakens the LCR induced β-globin promoter activity. The role of the proximal CACCC box is further demonstrated by the studies in thalassemia patients which show clustering of point mutations in the proximal CACCC box and the TATA box, resulting in severely decreased β-globin expression. A point mutation in the distal CACCC box resulted in only a slight decrease in β-globin expression Weatherall et al. (1989) "The Hemoglobinopathies" In *The Metabolic Basis of Inherited Disease*, ed. Scriver, et al. 2281 –2339. New York: McGraw-Hill, 6th ed).

These results raise several questions about the signals that control globin gene regulation. For example, the presence of multiple copies of the CACCC box in the LCR itself raises the question of why an additional CACCC box in the minimal promoter is required. Similarly, because the promoter and its upstream region contain binding sites for transcription activators, it is unclear why the LCR is necessary. In vitro experiments on naked DNA have shown that transcription activators such as CACCC box binding factors recruit and stabilize preinitiation complex (PIC) and or RNA polymerase II holoenzyme through protein-protein interaction (Pugh and Tjian (1990) *Cell* 61:1187–97; Chiang and Roeder (1995) *Science* 267:5 31–6; Gill et al. (1994) *Proc Natl. Acad. Sci. USA* 91:192–6; Stargell and Struhl (1996) *Trends Genet.* 12:311–5; Struhl (1996) *Cell* 84:179–82). In chromatin, however, such transcription activators must compete with the histone octamers for the binding site. The success in such competition will depend on the local chromatin structure. Furthermore, as has been demonstrated with other transcription activators (Elefanty et al. (1996) *EMBO J.* 15: 319–33), the local concentration of CACCC box binding factors in vivo is likely to vary from one region of the nucleus to another and, as a result, the likelihood that a CACCC box is occupied will also likely depend on its nuclear position. Therefore, in order to confer high level, position independent expression, the LCR must efficiently recruit transcription activators such as the CACCC box binding factor regardless of the local concentration and chromatin structure. Since the transcription factors and histones compete for DNA, the resulting high occupancy rate of the CACCC box should also prevent reformation nucleosome at the promoter region.

In order to understand the mechanism by which the LCR mediates the ε- to γ- to β-globin switches and position-independent expression of the β-globin genes, it is necessary to first understand, at the molecular level, how the LCR influences, if at all, the recruitment of the various polypeptides involved in β-globin gene expression (i.e. transcription activators and general transcription factors). However, for reasons discussed above, in vitro methods for analyzing protein-nucleic acid interactions do not accurately reflect the conditions that actually exist in vivo. To circumvent these shortcomings of previously available techniques, the strategy described herein which employs chimeric guide-endonucleases to analyze these interactions.

This Example describes the use of PINPOINT techniques to test the hypothesis that the globin LCR promotes efficient recruitment of the CACCC box binding factor to the human β-globin promoter. At least four polypeptides bind the CACCC box in erythroid cells; three of them, Sp1, BKLF and EKLF have been cloned (Kadonaga et al. (1987) *Cell* 51:1079–90; Crossley et al. (1996) *Mol Cell Biol.* 16:1695–705; Miller and Bieker (1993) *Mol Cell Biol.* 13: 2776–86). Proper expression of the β-globin gene requires EKLF, but it is not known whether this is a direct or indirect effect (Nuez et al. (1995) *Nature* 375:316–8; Perkins, et al. (1995) *Nature* 375:318–22). In cotransfection experiments, all three of these polypeptides can activate expression of the β-globin gene. Since Sp1 is the best characterized among these three factors, we have chosen to focus on in vivo recruitment of Sp1.

A. Material and Methods
1. Construction of Plasmids

A chimeric endonuclease that includes a FokI cleavage domain linked to a DNA binding domain from the transcription factor Sp1 was obtained as follows. A pCMV expression vector containing an Sp1-FokI fusion gene under the control of a CMV enhancer/promoter was constructed as follows. The cleavage domain of FokI restriction endonuclease (Li and Chandrasegaran (1993) *Proc Natl Acad Sci USA*

90:2764–8) was placed downstream of the pCMV enhancer/promoter. DNA encoding a nine glycine residues linker was inserted at the 5' end of the FokI fragment.

DNA fragments encoding various fragments of Sp1 were inserted into this vector upstream of the glycine linker and the cleavage domain of Fok I, under the operable control of the CMV promoter. A DNA fragment encoding Sp1 amino acids 83–685 (which includes the DNA binding domain) was inserted at the 5' end of the glycine linker. The vector pCMV-ABC Sp1-FokI was constructed by inserting DNA encoding Sp1 amino acids 83thr–530asp at the 5' end of the glycine linker. The D domain of Sp1 (620 gln through C-terminal) was inserted between ABC of Sp1 and FokI to obtain the pCMV-ABCD Sp1-Fok I expression vector. PCMV-AB Sp1-Fok I was created by deleting the region encoding the Sp1 C domain from pCMV-ABC Sp1-Fok I, in order to express the N-terminal to the 363 arg amino acid residue of Sp1. In another construct, a Ga14 binding domain was placed upstream of the glycine-encoding linker and the cleavage domain of FokI, to create Ga14-FokI.

For use as reporter genes, the human β-globin promoter (−374 to +21) was linked to a gene encoding chloramphenicol acetyltransferase (CAT). Various portions of the globin LCR were placed upstream of the β-globin promoter as follows. pHS234 (p269) was made by inserting upstream of the β-globin promoter a 4.63 kb HpaI to SalI fragment from pHS1234 (derived from LAR-β, see, Forrester et al. (1989) *Proc Natl acad Sci USA* 86:5439–43) that contains HS 2, 3, and 4 of the globin LCR. Additional LCR combination target DNAs were derived from pPN86 (Amrolia et al. (1995) *J Biol Chem* 270:12892–8): pHS23 was constructed by inserting a 0.85 kb SacI fragment from pHS1234 that included HS 3 into the SacI site of pPN86(HS 2) (Amrolia, Id.), pHS2,4 was constructed by inserting a 1.25 kb SacI fragment of HS4 from pHS1234 which was blunt-ended by Klenow fragment, into the XhoI site of pPN86 that also had been blunt-ended using Klenow fragment; pHS34 was constructed by inserting a 2.1 kb BamHI to SalI fragment of pHS1234 that contains HS3 and 4 into BglII-XhoI cleaved pPN86.

Promoter-deletion mutant target DNAs were constructed as follows. The promoter region was first sectioned as a GATA-1 binding site (−374 to −112), a CACCC binding site (−111 to −77), a CAAT box (−76 to −30), and a TATA box (−30 to +21). pHS234 was used as the wild type (GCCT), which contains each of these sections. PCR primers specific for each section were used to make the promoter deletion mutants. The "CCT" mutant, which contains a CACCC binding site, a CATTT box, and a TATA box, but lacks a GATA-1 binding site, was generated by inserting DNA fragments amplified from the this region of pHS234 using primer 2 (Region 2 linked to an 18 mer containing a NotI site; 5'-AAGGAAAAAAGCGGCCGC-3'(SEQ ID NO:1)) and JS52 (5'-CGTGGTATTCCTCCAGAGC GATGAAAAC-3' (SEQ ID NO:2)). The amplified fragment was digested with NotI and EcoRI and inserted into NotI- and EcoRI-digested pHS234.

The "CT" deletion mutant, which contained a CAT box and a TATA box, was made by inserting a DNA amplified using primer 3 (Region 3 linked to an 18mer NotI linker; (5'-AAGGAAAAAAGCGGCCGCGGCCAATCTACT CCCAGGAGCAG-3'; (SEQ ID NO:3)) and JS52 into the NotI and EcoRI sites of pHS234.

The "T" mutant, which contained only the TATA box, was created by inserting an amplified DNA obtained using primer 4 (Region 4 linked to an 18mer NotI linker; (5'-AAGGAAAAAAGCGGCCGCATAAAGTCAGGGCA GAGCCATCTAT-3'; (SEQ ID NO:4)) and JS52; the fragment was digested with NotI and EcoRI and inserted into NotI- and EcoRI-digested pHS234.

The "GCC" mutant, which had a GATA-1 binding site, a CACC binding site, and a CAT box, but lacked a TATA box, was generated by inserting a DNA amplified using primer 1 (5'-AAGGAAAAAAGCGGCCGCAGCTCTTCCACTT TTAGTGCAT-3'; (SEQ ID NO:5)) and primer 5 (Region 5 linked to nonamer containing EcoRI site; 5'-CCGGAATTCGCCCAGCCCTGGC-3' (SEQ ID NO:6)) that had been treated with NotI and EcoRI into NotI- and EcoRI-digested pHS234.

The "CC" mutant, which had a CACCC binding site and a CAT box, was constructed by inserting amplified DNA produced with Primers 2 and 5 that had been treated with NotI and EcoRI into NotI- and EcoRI-digested pHS234.

2. Transfections

Transient cotransfection of murine erythioleukemia (MEL) cells was performed with 1–10 μg of expression vector and 3–5 μg target DNA. Electroporation was performed at 975 μF, 250 V, and resistance level 5 (BTX Electro Manipulator 600) with about $10^7$ cells in 0.7 ml of Dulbecco modified Eagle medium without serum. The cells were immediately plated in 20 ml of DMEM containing 10% serum.

3. DNA Isolation and Analysis

DNA was isolated from transfected cells using the Hirt lysis procedure (See, e.g., Anant and Subramanian (1992) *Methods in Enzymology* 216: 20–29) 16–48 hour following transfection. Ligation-mediated PCR was performed as follows (see, e.g. Mueller and Wold (1989) *Science* 246: 780–686 for general protocol). DNA isolated from the cells was treated with the large fragment of DNA polymerase (New England Biolabs, Beverly Mass.) in a reaction mixture containing 33 mM each dNTP in order to generate blunt ends at the cleaved sites. Following phenol-chloroform extraction and filtration through Microcon-50™ (Amicon), blunt-ended DNA was purified. Linker LF1/JS21B (5'-GAAACACTTCAGATCTCCCGAGTCACCGC-3' (SEQ ID NO:7) annealed to 5'-phosphorylated GCGGTGACTCGGGAGATCTGAAGTG-3' (SEQ ID NO:8); 50 pmol) was ligated to blunt-ended sites using 4 U of T4 DNA ligase (NEB) at 16° C.

Ligation products were amplified by 25 cycles of PCR using linker-specific primer JS21B (5'-GAAACACTTCAGATCTCCCGAGTCACCGC-3' (SEQ ID NO:9)) plus a target-specific primer JS52 (5'-CGTGGTATTCACTCCAGAGCGATGAAAAC-3' (SEQ ID NO:10)) within the CAT gene. DNA was completely denatured for 3 min at 95° C. immediately before PCR. Each cycle comprised 15 s at 94° C., 30 s at 69° C., and 45 s at 72° C. (in a Power Block System™ of Ericomp located in San Diego, Calif.). One final cycle of extension reaction was done for 7 min at 72° C. The PCR products were run on the Nusieve™ 3:1 agarose gel (Rockland Md.) at 4.5–5.0 V/cm for 4 hour and transferred to Hybond-N+ (Amersham, Arlington Heights, Ill.). Southern hybridization was carried out at 52° C. with QuikHyb™ Hybridization Solution (Stratagene, La Jolla, Calif.). Southern blots were probed with a 17 bp CAT gene fragment (JS14; GTGAATAAAGGCCGGAT-3' (SEQ ID NO:11)).

Primer extension analysis was performed using 5'-end-labelled JS42 (TACGATGCCATTGGGATATATCAA CGGTGG-3' (SEQ ID NO:12)) as a primer; this sequence is found at the 3' end of the β-globin promoter. Because GCC and CC promoter deletion mutants do not include the region to which JS42 would hybridize, another primer (JS52;

5'-CGTGGTATTCACTCCAGAGCGATGAAAAC-3' (SEQ ID NO:13)) was used for primer extension of all promoter deletion mutants. Template DNA was completely denatured by heating with 10% DMSO at 94° C. for 2–3 min and quickly cooling on the dry ice. One cycle of primer extension was performed for 5 min at 94° C., 5 min at 70° C., and 5 min at 72° C., with Vent™ Exonuclease- Polymerase (New England Biolabs, Beverly, Mass.). The extended products were run on a 6% TBE-Urea sequencing gel (National Diagnostics, Atlanta, Ga.) at 70 Watts. DNA treated with HindIII or EcoRI was used for quantitation of recovered DNA following Hirt lysis by primer extension. cl
B. PINPOINT analysis of Sp1 Recruitment to β-globin LCR To test the hypothesis that the globin LCR recruits Sp1 to the β-globin promoter requires the capability to visualize in vivo protein-DNA interactions. Toward this end, the inventor developed a strategy referred to as PINPOINT-1 (Protein Position Identification with Nuclease Tail-1). This strategy makes use of the chimeric endonucleases described herein. In the experiments described in this Example, an expression vector that encodes a chimeric endonuclease composed of the Sp1 transcription factor linked to the nuclease domain of type IIS endonuclease FokI via a flexible linker, was transfected into MEL (murine erythroleukemic line) cells, along, with target DNA. FokI has a DNA binding domain which binds to the recognition sequence for the enzyme, and an independent nuclease domain which makes a double strand cut at a defined distance, 9 bp for one strand and 13 bp for the other, to one side of the recognition site (Li and Chandrasegaran, supra). The Sp1-FokI fusion protein, which is termed the Sp1 "pointer," competes with the endogenous pool of Sp1 and the other CACCC box factors in binding to the CACCC site in the β-globin promoter. If the Sp1 pointer binds to the CACCC box, the attached nuclease will cleave the nucleic acid near the binding site. Because the nuclease domain of FokI does not have sequence specificity of its own, the position and the probability of the cleavage is determined by the position of the linked Sp1 and its lingering time at that position, respectively. The target DNA, both cleaved and uncleaved, was harvested using the Hirt procedure and the position of the nuclease-induced cleavage was analyzed by primer extension directly, or by ligation mediated PCR followed by primer extension with radioactively labeled internal primer.

1. The LCR Helps to Recruit Sp1 to the β-globin Promoter

To determine whether the β-globin LCR plays a role in recruiting Sp1 to the β-globin promoter, an Sp1 pointer-expressing vector was cotransfected with one of two target plasmids: p269, which contains the human β-globin promoter joined to 5'HS 2,3 and 4 of the human β-globin LCR; and p306, which contains the β-globin promoter joined to a fragment of S phage DNA, as control. The 5' HS 1 was not included in the LCR fragment because its deletion in a patient did not affect β-globin gene expression. Sp1 (Kadonaga et al. (1987) Cell 51:1079–90; Kadonaga et al. (1988) Science 242:1566–70; Pascal and Tjian (1991) Genes Dev 5:1646–56) is linked to the nuclease. Low molecular weight DNA was harvested from transfected cells after 16 to 48 hours, and cleavage was detected using primer extension. The Sp1 pointer cleaves within the β-globin promoter much more efficiently (greater than 20 fold) when the promoter is joined to the LCR than when the promoter was joined to S phage DNA. The Sp1 pointer cleavage sites are located 5 bps upstream and 10 bps downstream of the double CACCC site in the β-globin promoter.

The simplest interpretation of this finding is that the LCR promotes recruitment of the Sp1 pointer to the β-globin promoter, but other explanations are possible. The LCR containing target DNA, which is supercoiled when transfected, could be relaxed or linearized more efficiently than the control target DNA. This might result if endogenous nucleases and/or Sp1 pointer is recruited efficiently to the LCR (which contains a number of Sp1 binding sites). If the nuclease domain of FokI is sensitive to the superhelicity of the target DNA, as some endonucleases are, it is possible that the control target DNA will not be cleaved as well as the LCR-containing target DNA even though the Sp1 pointer was recruited to the promoter of the control DNA equally as well as to the LCR containing target DNA. To examine this possibility, the target DNAs were maximally relaxed with topoisomerase I before transfection. Again, the LCR-containing target DNA was cleaved at the promoter much more efficiently than the control target DNA, ruling out the possibility that DNA topology was responsible for the difference in cleavage.

These results collectively support the hypothesis that the LCR recruits Sp1 to the β-globin promoter of a transfected target DNA. The experiments may mimic recruitment that occurs during a brief window of time during which the endogenous β-globin gene is being replicated and thus is free of histones. Newly replicated DNA is thought to be free of histones immediately following passage of the DNA replication fork, so just after replication of the β-globin locus transcription factor recruitment could take place.

MEL cells can be induced to differentiate and express high levels of the β-globin gene with DMSO. DMSO induction was tested for enhanced recruitment of Sp1 pointer to target DNAs with or without the LCR, but was found to not enhance recruitment. This suggests that DMSO induction affects another step in the process leading to high levels of the β-globin gene transcription. Such step might be part of the formation of the preinitiation complex (PIC) or a postinitiation process such as phosphorylation of the carboxy terminal domain (CTD) of the RNA polymerase II which is thought to stimulate elongation.

Since Sp1 easily forms a homotypic multimer, most likely a tetramer, an Sp1-DNA complex may be composed of two types of Sp1: those that are directly bound to DNA and those that are tethered through Sp1—Sp1 interaction (see also, Pascal and Tijian, supra.). Three Sp1 regions, A, B and D participate in this interaction. The cleavage pattern reflected the recruitment of both Sp1 types, since the Sp1 pointer used contains the domain for DNA binding as well as Sp1—Sp1 interaction. As a result, these experiments did not demonstrate precisely which type of Sp1 pointer is actually cleaving the DNA. In order to determine whether the LCR enhances the recruitment of the tethered Sp1, we repeated the experiment with Sp1 pointers that lacked the DNA binding domain but contained domains A, B, C or A, B, C and D. Since these pointers cannot bind to the DNA directly, its recruitment depended on protein-protein interaction with Sp1 already bound to DNA.

As with the Sp1 pointer containing the DNA binding domain, the tethered Sp1 pointer cleaved within the β-globin promoter much more efficiently when the promoter was joined to the LCR than to S phage DNA. This finding suggests that the LCR enhances the recruitment of tethered Sp1, and as a result, the formation of a multimeric Sp1 complexes on the promoter. Such formation should amplify the activation signal from one Sp1 binding site by a factor of four, or possibly multiples of four, if multiple tetramers are recruited. The cleavage site of the Sp1 pointers without the DNA binding domain is near the TATA box, whereas that of the intact Sp1 pointer is near the CACCC box. Therefore, it is likely that the cleavage pattern of the intact Sp1 pointer reflects that of the DNA-bound Sp1. Further deletions of the glutamine rich domains A and B or domain C resulted in no detectable cleavage, suggesting that these domains are important for the LCR enhanced recruitment.

2. The CACCC and TATA Boxes are Important for Sp1 Recruitment

The results discussed above demonstrate that the LCR plays an important role in the recruitment of Sp1 pointer. To further dissect the sequences required for Sp1 recruitment, the following experiments examined the roles of the CACCC and TATA boxes in Sp1 recruitment. A deletion of either box resulted in the loss of the LCR-enhanced recruitment. Thus, the LCR and TFIID domains worked together in recruiting Sp1 to the CACCC site. Since Sp1 has been shown to interact with hTAFII55 and dTAFII110 in vitro, these are the most likely components of TFIID to participate in the recruitment. Since the recruitment of TFIID is thought to be downstream of the recruitment of transcription activators such as Sp1, these results indicate that the TFIID complex formed on the TATA box stabilizes the Sp1 complex. Since other general transcription factors such TFIIA and B also bind near the TATA box, they might also participate in this interaction. Sp1 pointers lacking the DNA binding domain, however, are not recruited to the promoter region without the additional sequence upstream of the CACCC site (UCAC) which contains binding sites for CAAT, NF1 and GATA-1. This finding suggests that tethered Sp1, unlike DNA bound Sp1, needs additional interactions with factors binding upstream of the CACCC site.

Each of the core regions of 5' HS2, 3 and 4 contain multiple binding sites for NFE-2, GATA-1, E and CACCC box proteins. The results discussed herein support the hypothesis that, through Sp1-Sp1 and Sp1-GATA-1 interactions which are known to occur, LCR recruits Sp1 or perhaps more importantly, multimeric Sp1 complex to the CACCC site in the promoter. This complex is further stabilized by interaction with the general transcription machinery (e.g. TFIID) as well as transcription factors bound upstream of the CACCC site. One clear implication of these experiments is that the binding affinity of a protein for a DNA recognition site by itself is not a good indicator of whether it binds the DNA in the complex milieu that exists in a cell; other protein-protein interactions such as that with other transcription factors, the general transcription machinery, the chromatin components and nuclear matrix, and spatial compartmentalization within the nucleus are likely to play important roles in determining whether a protein is ultimately recruited to a particular DNA sequence. The PINPOINT technology provides a method of analyzing the effect of such interactions.

3. Individual Hypersensitive Sites Cooperate to Recruit Sp1 Pointer

The individual hypersensitive sites of the LCR act synergistically to confer high position independent expression. To determine whether recruitment of Sp1 pointer to the β-globin promoter is dependent on such synergy, target DNAs having one or more hypersensitive sites deleted were tested for ability to recruit Sp1 pointer. Deletion of a single hypersensitivity site resulted in a significant reduction of Sp1 pointer recruitment to the promoter. A combination of hypersensitivity sites 2 and 4 resulted in better recruitment than 2 and 3 or 3 and 4, but not as well as 2, 3 and 4. This finding is consistent with the notion that synergistic recruitment of Sp1 to the promoter plays a key role in the LCR mediated expression.

4. Enhanced Sp1 Recruitment Not a General Property of Enhancers

To examine whether recruitment of transcription activators such as Sp1 is a general property of enhancers, the LCR (p269) was compared to three copies of SV40 enhancer (p399) in their abilities to activate β-globin expression and to recruit Sp1. In transient transfection, the LCR and SV40 enhancers activate β-globin expression to similar levels. However, the SV40 enhancers do not appear to recruit Sp1 in the PINPOINT assay. Therefore, the strength of an enhancer does not always correlate with its ability to recruit transcription activators such as Sp1. This observation supports the hypothesis that one of the ways the LCR confers position independence is by recruiting transcription activators such as Sp1 to the promoter, which then participates in recruiting and stabilizing the general transcription factors near the TATA box. Consistent with this finding, the SV40 enhancer cannot confer position independence in transgenic mice. The results discussed herein, taken together with recent evidence that certain transcription activators promote RNA elongation (Blair et al. (1996) *EMBO J.* 15:1658–65), cis-acting elements such as enhancers, LCRs or silencers are likely to function at various levels from recruitment of transcription activators such as Sp1 to stabilization of general transcription machinery to processivity of RNA polymerase. These elements may also recruit chromatin organizing complexes such as SWI/SNF (Peterson and Tamkun (1995) *Trends Biochem Sci* 20: 143–6) and NURF (Tsukiyama et al. (1995) *Cell* 83: 1021–6) which then affect transcription factor recruitment and RNA elongation. Recent observations suggest that splicing factors are recruited to the site of transcription. The PINPOINT technology makes it possible to test whether the LCR plays a role in post-transcriptional modification such as splicing and polyadenylation by recruiting complexes involved in these processes.

This example demonstrates that the PINPOINT technology described herein is useful for studying the interaction between protein and nucleic acids. The technology was used to analyze the role of the β-globin LCR in the recruitment of transcription factors such as Sp1 to the β-globin promoter in living MEL cells. The results of these studies demonstrate that, on a transfected plasmid, the LCR enhances Sp1 recruitment and multimer formation on the β-globin promoter. The recruitment requires the cooperation of other transcription factors bound at the promoter region including TFIID. Based on these findings, a model is proposed in which LCR-bound Sp1 and GATA-1, and perhaps other factors, recruit Sp1 to the CACCC site in the promoter. Since the TATA box is also required for the LCR enhanced recruitment, TFIID and or TFIID associated factors are likely to stabilize recruited Sp1 or multimeric complexes of Sp1. Such Sp1 recruitment appears to be mediated through protein-protein interaction involving the glutamine-rich A and B domains and the C domain.

It is possible that the LCR also recruits chromatin remodeling complexes such as SWI/SNF or NURF to facilitate Sp1 recruitment if the promoter region is in a nucleosome. Indeed, preliminary results indicate that a mammalian SWI complex, BRG1, is recruited to the β-globin promoter by the LCR. β-globin gene expression is very dependent on the site of integration in transgenic mice, but is position independent when the gene is linked to the LCR. Such position dependence might be a result of different chromatin structure and local concentration of transcription factors throughout the genome. Thus, the LCR, by recruiting chromatin remodeling complexes such as that of BRG1, appears to open chromatin and recruit transcription activators, which in turn help recruit the general transcription machinery. Such LCR-mediated recruitment should help in keeping the promoter region nucleosome-free regardless of the local chromatin structure.

The PINPOINT technology described herein can also be used to address additional questions regarding the role of the LCR in β-globin gene expression. For example, one can use the technology to determine whether the LCR enhances recruitment of transcription factors to the endogenous β-globin promoter. Also, the technology can be used to determine whether additional CACCC box binding factors, such as EKLF and BKLF, also are recruited by the LCR and if so, which one is most likely to bind the β-globin CACCC box. One can also use the PINPOINT technology to determine whether the globin LCR recruits chromatin remodeling complexes such as BRG1 (or NURE) or histone modifying enzymes such as histone acetyl transferases (Roth and Allis (1996) *Cell* 87: 5–8), both of which should enhance recruitment of transcription factors.

In one embodiment, an in situ thermal cycler is used to amplify cleaved target nucleic acids. Where multiple sites are cleaved, the positions on the nucleic acids are optionally assessed by microscopy, or by any of the PCR detection, cloning or sequencing protocols described.

Example 9

Preparation of FLASHPOINT Reagents

This Example describes the preparation of a reagents that are useful in the FLASHPOINT methods of the invention. These reagents include an IMMUNOPOINTER, which consists of a micrococcal nuclease tethered to an immunoglobulin, as well as a molecular beacon conjugated to an antibody.

Preparation of an IMMUNOPOINTER

An expression vector for a fusion protein containing the flexible polypeptide linked to the micrococcal nuclease was constructed as follows. The coding region of the micrococcal nuclease was amplified by polymerase chain reaction using primers JC373 (5'-TGAAGACGAATTCACCGGTGCAACT-TCAACTAAAAAATTACATAAAGAACCTGCGACTTTAATTAAAGCGATTGATGGTGAGACGGT-3'; (SEQ ID NO:14)) and JC374 (5'-GACGACGGATCCGGAAGCGGCCGCTTGACCTGAATCAGCGTTGTC-3'; (SEQ ID NO:15)), which introduced SgrA1 and BspE1 cleavage sites in the 5' and 3' ends, respectively. Because JC373 included an ASP21 to GLU21 mutation, the amplified micrococcal nuclease also contained this mutation. The amplified fragment was cleaved with SgrA1 and BspE1 and cloned into SgrA1 and BspE1 sites of p461, which is a pBluescript2-based vector containing a humanized micrococcal nuclease (MNase) structural gene into which one can clone a guide domain. To construct a chimeric endonuclease, a guide domain coding region is placed upstream of the MNase structural gene and downstream of a CMV promoter. A polylinker is present at position 1245 for insertion of the guide domain fragment. The nucleotide sequence of p461 (SEQ ID NO:19) is provided as SEQ ID NO:19 in commonly assigned U.S. patent application Ser. No. 08/825,664, which was filed on Apr. 3, 1997.

The resulting plasmid (p566) was cleaved with SmaI and a linker (JC375; 5'-GCAACCCATGGGTTGC-3'; (SEQ ID NO:16)) was ligated to the blunt ends. Ligation of the linker introduced an NcoI site and a cysteine residue in frame immediately 5' to the flexible polypeptide. A DNA fragment encoding the flexible polypeptide-micrococcal nuclease fusion protein (hence forth called the nuclease tail) was isolated by cleaving the linker-ligated fragment with NcoI and NotI and cloned into a bacterial expression vector pET22b(+) (Novagen). The resulting plasmid (p616) was introduced into BL21(DE3) competent *E. coli* cells (Novagen) for the expression of the micrococcal nuclease tail containing the GLU21 mutation (Serpersu et al. (1987) *Biochemistry* 26: 1289–300).

In order to express micrococcal nuclease tail with ASP21 (wild type), GLU21 in p616 was converted to ASP21 by PCR amplifying the region containing the codon for amino acid 21 in p616 with primers JC396 (5'-TGCGGGGACTCGAGTCTGCA-3'; (SEQ ID NO:17)) and JC397 (5'-GACCTTTGTACATTAATTTAACCGTATCACCATCAATCGCT-3'; (SEQ ID NO:18)), cleaving the amplified fragment with SgrA 1 and BsrG 1 and cloning it into p616. The resulting plasmid, p684, was introduced into BL21(DE3) competent *E. coli* cells for the expression of the wild type micrococcal nuclease tail. The amino acid numbering scheme is based on that of micrococcal nuclease secreted from *Staph. aureus* (Shortle (1983) *Gene* 22: 181–9).

BL21 (DE3) *E. coli* cells transformed with the expression vectors described above were grown in LB and induced with IPTG. After induction, cells were collected by centrifugation at 5000×g for 5 min. The cell pellet was resuspended in 1× binding buffer (5 mM imidazole, 800 mM NaCl and 20 mM Tris-HCl pH 7.9) and sonicated. The lysate was centrifuged at 39,000×g for 20 minutes to remove debris. The nuclease tail, which contains 6 histidine residues at the carboxy terminus was then purified by $Ni^{2+}$ column chromatography.

Crosslinking the Nuclease Tail to Antibody (IMMUNOPOINT)

The nuclease tail, purified as described above, was reduced by incubating it with 100 mM DTT in PBS (phosphate-buffered saline) at 37° C. for 30 minutes. Reduced nuclease tail was desalted into PBS containing 5 mM EDTA. The antibody (0.5–1.0 mg) to be crosslinked to the nuclease tail was treated with 50–500 mg SMCC (succinimidyl 4-(N-maleimidomethyl) cyclohexane-1-carboxylate, Pierce Chemical Company, Rockford, IL) in 500 ml of PBS for 30 minutes at 37° C. The SMCC treated antibody was desalted into PBS. Desalted nuclease tail (at greater than four fold excess) and SMCC crosslinked antibody were incubated together at 4° C. overnight. The antibody crosslinked to the nuclease tail (IMMUNOPOINTER) was further purified with $Ni^{2+}$ column chromatography and or protein A/G affinity matrix (Pierce Chemical Company). Other proteins may be crosslinked to the nuclease tail in a similar manner. The crosslinked nuclease is activated by adding 1 mM $CaCl_2$ for 1 to 10 minutes.

Attachment of Molecular Beacon to Antibody

Equal concentrations of an antibody and a molecular beacon molecule (synthesized by CyberSyn, Lenni, Pa.) were mixed with BS3 (Bis(sulfosuccinimidyl) suberate, Pierce Chemical Company) in pH 7.5 PBS. When the protein concentration is above 5 mg/ml, 10-fold molar excess of the crosslinker (BS3) over the protein was used; when the protein concentration was below 5 mg/ml, 20- to 50-fold molar excess of the crosslinker was used. The reaction mixture was incubated at room temperature for 30 minutes or on ice for 2 hours. The reaction is quenched for 30 minutes with a Tris or glycine buffer, or with a buffer containing lysine (20–50 mM). Other proteins may be crosslinked to a beacon molecule in a similar manner.

All publications and patent applications cited in this specification are herein incorporated by reference as if each individual publication or patent application were specifically and individually indicated to be incorporated by reference in its entirety for all purposes. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the following claims.

What is claimed is:

1. A method of detecting whether a first molecule is in close proximity to a second molecule, the method comprising the steps of:
    attaching a molecular beacon to the first molecule, wherein the molecular beacon comprises an oligonucleotide to which is attached a fluorophore and a quencher;
    attaching an endonuclease moiety to the second molecule; and
    determining whether the first molecule is in close proximity to the second molecule by detecting whether fluorescence is emitted by the fluorophore, wherein fluorescence emission is indicative of cleavage of the oligonucleotide by the endonuclease moiety, thereby causing separation of the fluorophore and the quencher.

2. The method of claim 1, wherein either or both of the first molecule and the second molecule are located in a cell.

3. The method of claim 1, wherein either or both of the first molecule and the second molecule are located in an organism.

4. The method of claim 1, wherein the target molecule is present in a tissue sample.

5. The method of claim 1, wherein the molecular beacon is covalently attached to the first molecule.

6. The method of claim 1, wherein the molecular beacon is noncovalently attached to the first molecule.

7. The method of claim 6, wherein the molecular beacon is attached to a binding moiety which binds to the first molecule.

8. The method of claim 7, wherein the binding moiety is an antibody.

9. The method of claim 1, wherein the endonuclease moiety is covalently attached to the second molecule.

10. The method of claim 1, wherein the endonuclease moiety is noncovalently attached to the second molecule.

11. The method of claim 10, wherein the endonuclease moiety comprises a binding moiety which binds to the second molecule.

12. The method of claim 11, wherein the binding moiety is an antibody.

13. The method of claim 1, wherein the first molecule and the second molecule are separated by about ten nanometers or less before endonuclease cleavage.

14. The method of claim 13, wherein the first molecule is in contact with the second molecule before endonuclease cleavage.

15. The method of claim 1, wherein the endonuclease moiety comprises a calcium-inducible endonuclease, and the method further comprises the step of contacting the endonuclease moiety with calcium.

16. The method of claim 1, wherein the first molecule comprises a first member of a binding pair and the second molecule comprises a second member of the binding pair, and wherein the binding pair is selected from the group consisting of: enzyme:substrate, hormone:ligand, drug:receptor, protein:protein, protein/modifier, protein:nucleic acid; and nucleic acid:nucleic acid.

17. The method of claim 1, wherein the emission of fluorescence is detected by fluorescent microscopy or fluorometry.

18. A method of detecting a target molecule, the method comprising:
    contacting the target molecule with a chimeric fusion molecule that comprises an endonuclease molecule and a guide molecule that binds to the target molecule, thus guiding the chimeric fusion molecule to the target molecule;
    contacting the chimeric endonuclease with a molecular beacon comprising an oligonucleotide to which is attached a fluorophore and a quencher; and
    detecting the presence of a fluorescent signal which results from cleavage of the oligonucleotide by the endonuclease, thereby allowing separation of the quencher from the fluorophore.

19. The method of claim 18, wherein the target molecule is present in a cell.

20. The method of claim 18, wherein the target molecule is present in a tissue sample.

21. The method of claim 18, wherein the fluorescent signal is integrated over time.

22. The method of claim 18, wherein the chimeric endonuclease comprises a calcium-inducible endonuclease moiety, and the method further comprises the step of contacting the endonuclease moiety with calcium.

23. The method of claim 18, wherein the chimeric fusion molecule binds directly to the target molecule.

24. The method of claim 23, wherein the target molecule is a nucleic acid and the chimeric fusion molecule comprises a nucleic acid binding domain.

25. The method of claim 18, wherein the chimeric fusion molecule binds indirectly to the target molecule.

26. The method of claim 25, wherein a primary binding moiety binds to the target molecule and the chimeric fusion molecule binds to the primary binding moiety.

27. The method of claim 26, wherein the primary binding moiety is an antibody that binds to the target molecule and the chimeric fusion molecule comprises a moiety that binds to the antibody.

* * * * *